US009416069B2

United States Patent
Sita et al.

(10) Patent No.: US 9,416,069 B2
(45) Date of Patent: *Aug. 16, 2016

(54) SCALABLE PRODUCTION OF PRECISION HYDROCARBONS FROM TRIALKYLALUMINUM VIA TERNARY LIVING COORDINATIVE CHAIN TRANSFER POLYMERIZATION

(75) Inventors: Lawrence R. Sita, Silver Spring, MD (US); Jia Wei, Beltsville, MD (US)

(73) Assignee: University of Maryland, College Park, College Park, MD (US)

( * ) Notice: Subject to any disclaimer, the term of this patent is extended or adjusted under 35 U.S.C. 154(b) by 761 days.

This patent is subject to a terminal disclaimer.

(21) Appl. No.: 13/520,389

(22) PCT Filed: Jan. 4, 2011

(86) PCT No.: PCT/US2011/020116
§ 371 (c)(1),
(2), (4) Date: Jan. 11, 2013

(87) PCT Pub. No.: WO2011/082418
PCT Pub. Date: Jul. 7, 2011

(65) Prior Publication Data
US 2013/0109900 A1    May 2, 2013

Related U.S. Application Data

(60) Provisional application No. 61/292,045, filed on Jan. 4, 2010.

(51) Int. Cl.
*B01J 21/00* (2006.01)
*C07C 2/30* (2006.01)
*C08F 10/00* (2006.01)

(52) U.S. Cl.
CPC . *C07C 2/30* (2013.01); *C08F 10/00* (2013.01); *C08F 2410/01* (2013.01); *C08F 2420/04* (2013.01)

(58) Field of Classification Search
CPC ... C07C 2/30; C08F 2410/01; C08F 2420/04; C08F 10/00
USPC .......................................................... 585/506
See application file for complete search history.

(56) References Cited

U.S. PATENT DOCUMENTS

| 6,339,128 B1 * | 1/2002 | Nakayama et al. ........... 525/191 |
| 2003/0114623 A1 * | 6/2003 | Mitani .................... C08F 10/00 526/352 |

FOREIGN PATENT DOCUMENTS

| WO | WO 2006/101596 A1 | 9/2006 |
| WO | WO 2008/027283 A2 | 3/2008 |
| WO | WO 2009/061499 A1 | 5/2009 |

OTHER PUBLICATIONS

Zhang, W. "Living Coordinative Chain Transfer Polymerization of 1-Alkenes." Ph.D. Dissertation, University of Maryland, College Park, MD, 2008.*

(Continued)

*Primary Examiner* — In Suk Bullock
*Assistant Examiner* — Aaron Pierpont
(74) *Attorney, Agent, or Firm* — Sterne, Kessler, Goldstein & Fox PLLC

(57) ABSTRACT

Disclosed is a method of producing a polyolefin composition comprising contacting a metallocene pre-catalyst, a co-catalyst, a primary surrogate, and a secondary surrogate; adding a first olefin monomer; and polymerizing the first monomer for a time sufficient to form the polyolefin. Also disclosed is a method of producing a block polyolefin composition comprising contacting a metallocene pre-catalyst, a co-catalyst, a primary surrogate, and a secondary surrogate; polymerizing the first monomer for a time sufficient to form the polyolefin; adding a second monomer; and polymerizing the second olefin monomer for a time sufficient to form said block polyolefin composition. The method allows for the production of polyolefins of low molecular weights and narrow molecular weight distributions.

29 Claims, 11 Drawing Sheets

(56) References Cited

OTHER PUBLICATIONS

Alfano, F., et al., "Polypropylene "Chain Shuttling" at Enantiomorphous and Enantiopure Catalytic Species: Direct and Quantitative Evidence from Polymer Microstructure," *Macromolecules* 40:7736-7738, American Chemical Society, United States (2007).
Arriola, D. J., et al., "Catalytic Production of Olefin Block Copolymers via Chain Shuttling Polymerization," *Science* 312:714-719, American Association for the Advancement of Science, United States (2006).
Bazan, G.C., et al., "Catalytic Insertion of Ethylene into Al—C Bonds with Pentamethylcyclopentadienyl-Chromium (III) Complexes," *Organometallics* 20:2059-2064, American Chemical Society, United States (2001).
Britovsek, G.J.P., et al., "Iron-Catalyzed Polyethylene Chain Growth on Zinc: Linear α-Olefins with a Poisson Distribution," *Angew. Chem. Int. Ed.* 41(3):489-491, Wiley-VCH, Germany (2002).
Britovsek, G.J.P., et al., "Iron Catalyzed Polyethylene Chain Growth on Zinc: A Study of the Factors Delineating Chain Transfer *versus* Catalyzed Chain Growth in Zinc and Related Metal Alkyl Systems," *J. Am. Chem. Soc.* 126:10701-10712, American Chemical Society, United States (2004).
Chenal, T., et al., "Controlled polyethylene chain growth on magnesium catalyzed by lanthanidocene: A living transfer polymerization for the synthesis of higher dialkyl-magnesium," *Polymer* 48:1844-1856, Elsevier Ltd., Netherlands (2007).
Cheng, H.N., "Comonomer sequence distribution in ethylene/1-hexene copolymers," *Polymer Bulletin* 26:325-332, Springer-Verlag, Germany (1991).
Coates, G.W., et al., "Catalysts for the Living Insertion Polymerization of Alkenes: Access to New Polyolefin Architectures Using Ziegler—Natta Chemistry," *Angew. Chem. Int. Ed.* 41:2236-2257, Wiley-VCH, Germany (2002).
Domski, G.J., et al., "Living alkene polymerization: New methods for the precision synthesis of polyolefins," *Prog. Polym. Sci.* 32:30-92, Elsevier B.V., Netherlands (2007).
Ganesan, M., and Gabbaï, F.P., "[Cp*Cr($C_6F_5$)(Me)(Py)] as a Living Chromium(III) Catalyst for the 'Aufbaureaktion,'" *Organometallics* 23:4608-4613, American Chemical Society, United States (2004).
Ganesan, M., and Gabbaï, F.P., "Synthesis, structure and catalytic properties of [Cp*Cr($C_6F_5$)(Bn)(THF)] toward ethylene in the presence of AlEt$_3$," *Journal of Organometallic Chemistry* 690:5145-5149, Elsevier B.V., Netherlands (2005).
Harney, M.B., et al., "Discrete, Multiblock Isotactic-Atactic Stereoblock Polypropene Microstructures of Differing Block Architectures through Programmable Stereomodulated Living Ziegler—Natta Polymerization," *Angew. Chem. Int. Ed.* 45:2400-2404, Wiley-VCH, Germany (2006).
Harney, M.B., et al., "Bimolecular Control over Polypropene Stereochemical Microstructure in a Well-Defined Two-State System and a New Fundamental Form: Stereogradient Polypropene," *Angew. Chem. Int. Ed.* 45:6140-6144, Wiley-VCH, Germany (2006).
Hlatky, G.G., et al., "Ionic, Base-Free Zirconocene Catalysts for Ethylene Polymerization," *J. Am. Chem. Soc.* 111:2728-2729, American Chemical Society, United States (1989).
Hustad, P.D., et al., "Continuous Production of Ethylene-Based Diblock Copolymers Using Coordinative Chain Transfer Polymerization," *Macromolecules* 40(20):7061-7064, American Chemical Society, United States (2007).
Hustad, P.D. et al., "An Exploration of the Effects of Reversibility in Chain Transfer to Metal in Olefin Polymerization," *Macromolecules* 41(12):4081-4089, American Chemical Society, United States (2008).
Jayaratne, K.C., and Sita, L.R., "Stereospecific Living Ziegler—Natta Polymerization of 1-Hexene," *J. Am. Chem. Soc.* 122:958-959, American Chemical Society, United States (2000).
Jayaratne, K.C., et al., "Living Ziegler—Natta Cyclopolymerization of Nonconjugated Dienes: New Classes of Microphase-Separated Polyolefin Block Copolymers via a Tandem Polymerization/Cyclopolymerization Strategy," *J. Am. Chem. Soc.* 122:10490-10491, American Chemical Society, United States (2000).
Kaneyoshi, H., et al., "Synthesis of Block and Graft Copolymers with Linear Polyethylene Segments by Combination of Degenerative Transfer Coordination Polymerization and Atom Transfer Radical Polymerization," *Macromolecules* 38(13):5425-5435, American Chemical Society, United States (2005).
Keaton, R.J., et al., "Structural Characterization of Zirconium Cations Derived from a Living Ziegler—Natta Polymerization System: New Insights Regarding Propagation and Termination Pathways for Homogeneous Catalysts," *J. Am. Chem. Soc.* 122:12909-12910, American Chemical Society, United States (2000).
Keaton, R.J., et al., "Dramatic Enhancement of Activities for Living Ziegler—Natta Polymerizations Mediated by 'Exposed' Zirconium Acetamidinate Initiators: The Isospecific Living Polymerization of Vinylcyclohexane," *J. Am. Chem. Soc.* 123:6197-6198, American Chemical Society, United States (2001).
Kempe, R., "How to Polymerize Ethylene in a Highly Controlled Fashion?" *Chem. Eur. J.* 13:2764-2773, Wiley-VCH, Germany (2007).
Kretschmer, W.P., et al., "Reversible Chain Transfer between Organoyttrium Cations and Aluminum: Synthesis of Aluminum-Terminated Polyethylene with Extremely Narrow Molecular-Weight Distribution," *Chem. Eur. J.* 12:8969-8978, Wiley-VCH, Germany (2006).
Mani, G., and Gabbaï, F.P., "A Neutral Chromium(III) Catalyst for the Living Aufbaureaktion" *Angew. Chem. Int. Ed.* 43(17):2263-2266, Wiley-VCH, Germany (2004).
Matyjaszewski, K., "Introduction to Living Polymerization. Living and/or Controlled Polymerization," *Journal of Physical Organic Chemistry* 8:197-207, John Wiley & Sons, Ltd., United States (1995).
Müller, A.H.E., et al., "Kinetic Analysis of 'Living' Polymerization Processes Exhibiting Slow Equilibria. 1. Degenerative Transfer (Direct Activity Exchange between Active and 'Dormant' Species). Application to Group Transfer Polymerization," *Macromolecules* 28:4326-4333, American Chemical Society, United States (1995).
Pelletier, J.-F., et al., "Synthesis of New Dialkylmagnesium Compounds by Living.Transfer Ethylene Oligo- and Polymerization with Lanthanocene Catalysts," *Agnew. Chem. Int. Ed. Engl.* 35(16):1854-1856, Wiley-VCH, Germany (1996).
Périn, S.G.M., et al., "Unusual Effect of Diethyl Zinc and Triisobutylaluminium in Ethylene/1-Hexene Copolymerisation using an MgCl$_2$-Supported Ziegler-Natta Catalyst," *Macromol. Chem. Phys.* 207:50-56, Wiley-VCH, Germany (2006).
Quirk, R.P., and Lee, B., "Experimental Criteria for Living Polymerizations," *Polymer International* 27:359-367, Society of Chemical Industry, United Kingdom (1992).
Reybuck, S.E., et al., "Copolymerization Behavior of Unbridged Indenyl Metallocenes: Substituent Effects on the Degree of Comonomer Incorporation," *Macromolecules* 35:637-643, American Chemical Society, United States (2002).
Ring, J.O., et al., "Controlled Synthesis and Characterization of Poly[ethylene-*block*-(L,L-lactide)]s by Combining Catalytic Ethylene Oligomerization with "Coordination-Insertion" Ring-Opening Polymerization," *Macromol. Chem. Phys.* 208:896-902, Wiley-VCH, Germany (2007).
Rogers, J.S., and Bazan, G.C., "Oligomerization-transmetalation reactions of Cp*CrMe$_2$(PMe$_3$)/methylaluminoxane catalysts," *Chem. Commun.* 1209-1210, The Royal Society of Chemistry, United Kingdom (2000).
Sakuma, A., et al., "Living Olefin Polymerization and Block Copolymer Formation with FI Catalysts," *Polymer Journal* 39:193-207, The Society of Polymer Science, Japan (2007).
Suhm, J., et al., "Temperature Dependence of Copolymerization Parameters in Ethene/1-Octene Copolymerization Using Homogeneous *rac*-Me$_2$Si(2-MeBenz[e]Ind)$_2$ZrCl$_2$/MAO Catalyst," *Journal of Polymer Science: Part A: Polymer Chemistry* 35:735-740, John Wiley & Sons, Inc., United States (1997).
Van Meurs, M., et al., "Polyethylene Chain Growth on Zinc Catalyzed by Olefin Polymerization Catalysts: A Comparative Investigation of Highly Active Catalyst Systems across the Transition Series," *J. Am. Chem. Soc.* 127:9913-9923, American Chemical Society, United States (2005).

(56) References Cited

OTHER PUBLICATIONS

Ventolà, L., et al., "Molecular alloys as phase change materials (MAPCM) for energy storage and thermal protection at temperatures from 70 to 85° C.," *J Phys. Chem. Solids* 66:1668-1674, Elsevier, Netherlands (2005).

Zhang, W., and Sita, L.R., "Investigation of Dynamic Intra- and Intermolecular Processes within a Tether-Length Dependent Series of Group 4 Bimetallic Initiators for Stereomodulated Degenerative Transfer Living Ziegler—Natta Propene Polymerization," *Adv. Synth. Catal.* 350:439-447, Wiley-VCH, Germany (2008).

Zhang, Y., and Sita, L.R., "Solid-supported stereospecific living Ziegler—Natta polymerization of α-olefins," *Chem. Commun.* 2358-2359, The Royal Society of Chemistry, United Kingdom (2003).

Zhang, Y., et al., "Degenerative Transfer Living Ziegler-Natta Polymerization: Application to the Synthesis of Monomodal Stereoblock Polyolefins of Narrow Polydispersity and Tunable Block Length," *J. Am. Chem. Soc.* 125(30):9062-9069, American Chemical Society, United States (2003).

Zhang, Y., et al., "Goldilocks Effect of a Distal Substituent on Living Ziegler-Natta Polymerization Activity and Stereoselectivity within a Class of Zirconium Amidinate-Based Initiators," *Organometallics* 23:3512-3520, American Chemical Society, United States (2004).

Zhang, Y., and Sita, L.R., "Stereospecific Living Ziegler-Natta Polymerization via Rapid and Reversible Chloride Degenerative Transfer between Active and Dormant Sites," *J. Am. Chem. Soc.* 126(25):7776-7777, American Chemical Society, United States (2004).

Ziegler, K., et al., "Aluminum-organische Synthese im Bereich olefinischer Kohlenwasserstoffe," *Angew. Chemie* 64:323-329, Wiley-VCH, Germany (1952).

Abstract of Ziegler, K., et al., "Aluminum-organische Synthese im Bereich olefinischer Kohlenwasserstoffe," *Angew. Chemie* 64:323-329, Wiley-VCH, Germany (1952).

International Search Report for International Application No. PCT/US2011/20116, mailed Apr. 21, 2011, U.S. Patent and Trademark Office, Alexandria, VA.

\* cited by examiner

SCALABLE PRODUCTION OF PRECISION HYDROCARBONS FROM TRIALKYLALUMINUM VIA TERNARY LIVING COORDINATIVE CHAIN TRANSFER POLYMERIZATION

Part of the work performed during development of this invention utilized U.S. Government funds. The work was partly funded by the National Science Foundation Grant CHE0848293. The U.S. Government has certain rights in this invention.

BACKGROUND OF THE INVENTION

1. Field of the Invention

The present invention provides a method of producing a polyolefin composition comprising contacting a metallocene pre-catalyst, a co-catalyst, a primary surrogate, and a secondary surrogate; adding a first olefin monomer; and polymerizing the first monomer for a time sufficient to form the polyolefin. The present invention also provides a method of producing a block polyolefin composition comprising contacting a metallocene pre-catalyst, a co-catalyst, a primary surrogate, and a secondary surrogate; polymerizing the first monomer for a time sufficient to form the polyolefin; adding a second monomer; and polymerizing the second olefin monomer for a time sufficient to form said block polyolefin composition. The method allows for the production of polyolefins of low molecular weights and narrow molecular weight distributions.

2. Related Art

Several transition-metal-based catalysts have been reported that can mediate the living metal-mediated coordination polymerization (also known as homogeneous, single-site Ziegler-Natta polymerization) of ethene, propene, higher α-olefins, and α,ω-nonconjugated dienes, and, in some cases, these proceed with a high degree of stereocontrol (tacticity) ((for a review of catalysts for living coordination polymerization of ethene and α-olefins, see: Coates, G. W., et al., *Angew. Chem. Int. Ed.* 41:2236-2257 (2002)); (for the living and stereoselective coordination polymerization of α-olefins and α,ω-non-conjugated dienes, see: Jayaratne, K. C., et al., *J. Am. Chem. Soc.* 122:958-959 (2000)); Jayaratne, K. C., et al., *J. Am. Chem. Soc.* 122:10490-10491 (2000); Keaton, R. J., et al., *J. Am. Chem. Soc.* 123:6197-6198 (2001); Zhang, Y., et al., *Chem. Commun.* 2358-2359 (2003); Zhang, Y., et al., *Organometallics* 23:3512-3520 (2004); Harney, M. B., et al., *Angew. Chem. Int. Ed.* 45:2400-2404 (2006); Harney, M. B., et al., *Angew. Chem. Int. Ed.* 45:6140-6144 (2006); Zhang, W., et al., *Adv. Synth. Catal.* 350:439-447 (2008)). However, the commercialization of new polyolefin materials and products that take advantage of the unique capabilities of living coordination polymerizations appears unlikely ((for reviews of polyolefin materials prepared through living coordination polymerization, see: Domski, G. J., et al., *Prog. Polym. Sci.* 32:30-92 (2007); Sakuma, A., et al., *Polym. J.* 39:193-207 (2007)); Szwarc, M., et al., *Ionic Polymerization and Living Polymers*; Chapman & Hall: New York (1993); Quirk, R. P., et al., *Polym. Int.* 27:359-367 (1992); Matyjaszewski, K., *J. Phys. Org. Chem.* 8:197-207 (1995)).

The same fundamental criterion of a living polymerization, namely, chain-growth propagation in the absence of irreversible chain termination, serves to establish a 'one polymer chain per active metal center' cap on product yield as a critical liability. The severity of this liability sharply increases as the targeted number-average degree of polymerization, $X_n$, of the desired polyolefin product decreases. While living coordination polymerization is ideally suited for accessing the largely unexplored material science and technology associated with architecturally well-structured 'precision polyolefins' of very low to moderate molecular weights (ca 500-10,000 Da), the practical availability of significant quantities of these materials presently remains out of reach due to unfavorable weight (polymer) to weight (catalyst) ratios ((for a review of catalysts for living coordination polymerization of ethene and α-olefins, see Coates, G. W., et al., *Angew. Chem. Int. Ed.* 41:2236-2257 (2002)); (for reviews of polyolefin materials prepared through living coordination polymerization, see Domski, G. J., et al., *Prog. Polym. Sci.* 32:30-92 (2007); Sakuma, A., et al., *Polym. J.* 39:193-207 (2007)); Szwarc, M., et al., *Ionic Polymerization and Living Polymers*; Chapman & Hall: New York (1993); Quirk, R. P., et al., *Polym. Int.* 27:359-367 (1992); Matyjaszewski, K., *J. Phys. Org. Chem.* 8:197-207 (1995); Kaneyoshi, H., et al., *Macromolecules* 38:5425-5435 (2005); Ring, J. O., et al., *Macromol. Chem. Phys.* 208:896-902 (2007); Ventold, L., et al., *J. Phys. Chem. Solids* 66:1668-1674 (2005)).

International Application Publication No. WO 2009/061499 discloses the living coordinative chain-transfer polymerization and copolymerization of ethene, propene, long-chain α-olefins, α,ω-nonconjugated dienes using $\{\eta^5\text{-}C_5Me_5\}Hf(Me)[N(Et)C(Me)N(Et)]\}[B(C_6F_5)_4]$ as the active transition-metal initiator for chain-growth propagation with multiple stoichiometric equivalents of diethylzinc ($ZnEt_2$) as surrogate chain growth sites. Successful living coordinative chain-transfer polymerization of these monomers requires that the rate, and rate constant for reversible (polymeryl group) chain transfer between the active transition-metal propagating centers and the inactive surrogate main-group metal species, $v_{ct}$ and $k_{ct}$, respectively, should be far greater than the corresponding kinetic parameters for transition-metal-mediated propagation, $v_p$ and $k_p$, in order to insure that all active and surrogate species appear to propagate at the same rate.

The final yield of polyolefin product obtained through living coordinative chain-transfer polymerization is dependent only upon the initial volume of $ZnEt_2$ employed. Thus, living coordinative chain-transfer polymerization circumvents the "one-polymer-per-metal-center" criterion of traditional living coordination polymerizations that has proven to be an insurmountable liability to scalable production of precision polyolefins and precision hydrocarbons. However, from a cost and safety perspective, the transport and handling of industrial volumes of $ZnEt_2$ is problematic and accordingly, the dependence of a living coordinative chain-transfer polymerization method on $ZnEt_2$ may limit the commercialization of precision hydrocarbons and precision-hydrocarbon based products. Conversely, $AlEt_3$ and $Al(iso\text{-}butyl)_3$ can be produced on a commodity scale from aluminum powder, dihydrogen, and ethene or isobutene, respectively, and are significantly less expensive and substantially less pyrophoric in contact with air than $ZnEt_2$. Furthermore, if all three alkyl groups of these trialkylaluminums engage equally in rapid in reversible chain-transfer, trialkylaluminums have an additional advantage over $ZnEt_2$.

In 1952, Karl Ziegler introduced the Aufbaureaktion, a process by which the controlled oligomerization of ethene can be achieved using triethylaluminum, $AlEt_3$, as a chain-growth initiator at high pressure (about 100 psi) and at low temperatures (about 130° C.) (Ziegler, K., *Angew. Chemie* 64:323-329 (1952)). The process was commercially successful due to its ability to provide a pseudo-Poisson distribution of long-chain linear α-olefins of general formula $H_2C\!=\!C(C_{1\text{-}2})_nCH_3$ (n=1-15) and the corresponding saturated terminal alcohols, HOCH$_2$(CH$_2$)$_{n+1}$CH$_3$, through direct chemical transformations of Al[(CH$_2$)$_{n+2}$CH$_3$]$_3$ intermediates. In 2006, global production of long-chain linear α-olefins was four million metric tons, with 55% of this amount targeted for lubricants, plasticizers, detergents, additives, and fine chemicals. However, no Aufbaureaktion for the controlled oligomerization of propene or long chain α-olefins using AlEt$_3$ or other trialkylaluminums as a chain-growth initiator has been developed. Accordingly, the potential technological value of new classes of hydrocarbon-based products that might be available from such processes on a commodity volume scale remains unknown.

Precision hydrocarbons represent a new class of polyolefins that are distinguished by having programmable and architecturally-discrete carbon-carbon bonded frameworks, very low (e.g., oligomeric) molecular weights, and extremely narrow molecular weight distributions. It is believed that precision hydrocarbons could offer benefits to society as green and sustainable synthetic base stock oils and waxes for a broad range of technological applications.

It should be noted that it was not obvious that ZnEt$_2$ could be used to realize the goal of ternary living coordinative chain-transfer polymerization. It has previously been reported that, in solution, a 1:1 mixture of AlEt$_3$ and ZnEt$_2$ undergoes spontaneous decomposition to yield unidentifiable products (Périn, S. G. M., et al., *Macromol. Chem. Phys.* 207:50-56 (2006)). Additionally, the use of ZnEt$_2$ as both a secondary surrogate and as a chain-transfer mediator is mechanistically quite distinct from its role as a chain-shuttling agent for transfering a polymeryl group between two different active transition-metal propagating species as originally used for the production of blocky poly(ethene-co-octene) via a non-living process (Hustad, P. D., et al., *Macromolecules* 40:7061-7064 (2007)). It is believed that the use of two different main-group metal alkyl species that play different synergistic roles within the coordinative chain transfer polymerization of ethene, propene, or longer-chain α-olefins has not yet been reported.

There is a need, therefore, for new methods of coordination polymerization of olefins that allows for scalability of the volume of polyolefins that can be prepared through living polymerization with a dramatic reduction in the amount of transition metal catalyst that is required while not sacrificing all the desired beneficial features of the polymer that can be obtained through a living process, including tunable molecular weights, narrow polydispersities, ability to prepare block copolymers with discrete block junctions, random copolymers, and polyolefins with well-defined and discrete end-group functionalizations.

BRIEF SUMMARY OF THE INVENTION

The present invention provides a method of producing a polyolefin composition comprising contacting a metallocene pre-catalyst, a co-catalyst, a primary surrogate, and a secondary surrogate, adding a first olefin monomer; and polymerizing said first monomer for a time sufficient to form said polyolefin.

In one embodiment of the present invention, the primary surrogate is Al(R$^8$)$_3$, wherein R$^8$ is a C$_1$-C$_{10}$ alkyl. In another embodiment, the primary surrogate is selected from the group consisting of AlEt$_3$, AlMe$_3$, Al(iso-butyl)$_3$, Al(n-hexyl)$_3$, Al(n-propyl)$_3$, and Al(t-butyl)$_3$. In another embodiment, the primary surrogate is Al(iso-butyl)$_3$. In another embodiment, the primary surrogate is AlEt$_3$. In another embodiment, the primary surrogate is Al(n-propyl)$_3$.

In one embodiment of the present invention, the secondary surrogate is Zn(R$^9$)$_2$, wherein R$^9$ is a C$_1$-C$_{10}$ alkyl. In another embodiment, the secondary surrogate is selected from the group consisting of ZnMe$_2$, ZnEt$_2$, Zn(n-butyl)$_2$, Zn(isoamyl)$_2$, Zn(t-butyl)$_2$, Zn(neopentyl)$_2$, Zn(n-propyl)$_2$, and Zn(iso-propyl)$_2$. In another embodiment, the secondary surrogate is ZnEt$_2$.

In one embodiment of the present invention, the primary surrogate and the secondary surrogate are added in a primary surrogate:secondary surrogate ratio of about 1:1 to about 200:1. In another embodiment, the ratio is from about 1.1:1 to about 100:1. In another embodiment, the ratio is about 9:1. In another embodiment, the ratio is about 19:1.

In one embodiment of the present invention, the metallocene pre-catalyst is (η$^5$-C$_5$Me$_5$)Hf(Me)$_2$[N(Et)C(Me)N(Et)].

In one embodiment of the present invention, the co-catalyst is [PhNMe$_2$H][B(C$_6$F$_5$)$_4$], [PhNMe$_2$H][B(C$_6$F$_5$)$_3$Me], or B(C$_6$F$_5$)$_3$.

In one embodiment of the present invention, the primary surrogate and the secondary surrogate are contacted with the metallocene pre-catalyst and the co-catalyst in an inert solvent. In one embodiment, the solvent is toluene.

In one embodiment of the present invention, the primary surrogate, the secondary surrogate, the metallocene pre-catalyst, and the co-catalyst are contacted at a temperature of about −20° C. to about 25° C.

In one embodiment of the present invention, the first olefin monomer is ethene, propene, 1-butene, 1-pentene, 1-hexene, 1-heptene, 1-octene, styrene, butadiene, isoprene, 3-methylbutene, 3-methyl-1-pentene, vinylcyclohexane, vinylcyclobutane, vinylcyclopentane, vinylcyclooctane, 1-decene, enantiomerically pure β-citronellene, 3,5,5-trimethyl-1-hexene, cyclopentene, vinylcyclohexene or 4-methyl-1-pentene. In another embodiment, the first olefin monomer is ethene, propene, 1-hexene, 1-octene, or 1,5-hexadiene.

In one embodiment of the present invention, the polyolefin is an atactic polyolefin having a polydispersity index of about 1.01-1.15.

In one embodiment of the present invention, the metallocene pre-catalyst is (η$^5$-C$_5$Me$_5$)Hf(Me)$_2$[N(Et)C(Me)N(Et)], the primary surrogate is AlEt$_3$, the secondary surrogate is ZnEt$_2$, and the first olefin monomer is propene. In one embodiment, the ratio of AlEt$_3$ to ZnEt$_2$ is about 1:1.

In one embodiment of the present invention, the metallocene pre-catalyst is (η$^5$-C$_5$Me$_5$)Hf(Me)$_2$[N(Et)C(Me)N(Et)], the primary surrogate is Al(n-propyl)$_3$, the secondary surrogate is ZnEt$_2$, and the first olefin monomer is propene. In one embodiment, the ratio of Al(n-propyl)$_3$ to ZnEt$_2$ is about 1:1.

In one embodiment of the present invention, the metallocene pre-catalyst is (η$^5$-C$_5$Me$_5$)Hf(Me)$_2$[N(Et)C(Me)N(Et)], the primary surrogate is Al(iso-butyl)$_3$, the secondary surrogate is ZnEt$_2$, and the first olefin monomer is propene. In one embodiment, the ratio of primary surrogate:secondary surrogate is from about 1:1 to about 19:1. In another embodiment, the ratio of primary surrogate:secondary surrogate is from about 9:1 to about 19:1.

The present invention also provides a method of producing a polyolefin composition comprising contacting a metallocene pre-catalyst, a co-catalyst, a primary surrogate, and a secondary surrogate, adding a first olefin monomer; polymerizing said first monomer for a time sufficient to form said polyolefin; and further adding a second olefin monomer; and polymerizing said second monomer for a time sufficient to form said polyolefin.

In one embodiment of the present invention, the second olefin monomer is ethene, propene, 1-butene, 1-pentene, 1-hexene, 1-heptene, 1-octene, styrene, butadiene, isoprene, 3-methylbutene, 3-methyl-1-pentene, vinylcyclohexane, vinylcyclobutane, vinylcyclopentane, vinylcyclooctane, 1-decene, enantiomerically pure β-citronellene, 3,5,5-trimethyl-1-hexene or 4-methyl-1-pentene.

In one embodiment of the present invention, the polyolefin is an atactic living polyolefin. In another embodiment, the polyolefin comprises a diblock copolymer having the formula: atactic-poly(first olefin)-co-poly(second olefin). In another embodiment, the diblock copolymer composition has a polydispersity index of about 1.02-1.2. In another embodiment, the diblock copolymer is monomodal.

In one embodiment of the present invention, the metallocene pre-catalyst is $(\eta^5\text{-}C_5Me_5)Hf(Me)_2[N(Et)C(Me)N(Et)]$, the primary surrogate is $Al(iso\text{-}butyl)_3$, the secondary surrogate is $ZnEt_2$, the first olefin monomer is propene, and the second olefin monomer is 1-octene. In another embodiment of the invention, the metallocene pre-catalyst is $(\eta^5\text{-}C_5Me_5)Hf(Me)_2[N(Et)C(Me)N(Et)]$, the primary surrogate is $AlEt_3$, the secondary surrogate is $ZnEt_2$, the first olefin monomer is ethene, and the second olefin monomer is propene.

DETAILED DESCRIPTION OF THE INVENTION

Figure 1:
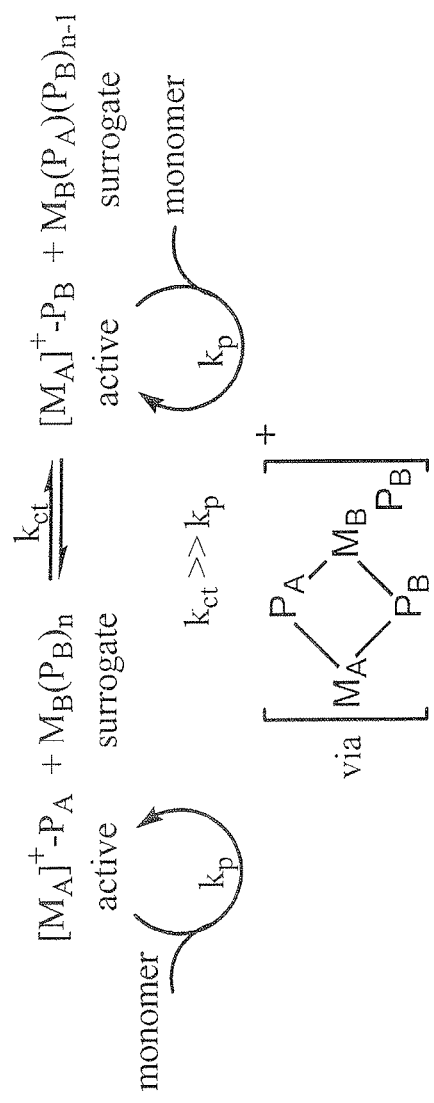
FIG. 1 shows the reversible chain ($P_A$ and $P_B$) transfer between active transition metal propagating centers ($M_A$) and chain-growth inactive main growth metal alkyl centers ($M_B$) of living coordinative chain-transfer polymerization.

"Metallocene" is used here to mean any organometallic coordination complex containing at least one or more σ-bonded or η"-bonded ligands coordinated with a metal atom from Groups IIIB to VIII or the Lanthanide series of the Periodic Table of the Elements. An example of a σ-bonded or η"-bonded ligand is the cyclopentadienyl ring. Examples of the metal atoms are the metals of Group IVB such as titanium, zirconium or hafnium.

A stereoregular macromolecule is understood to be a macromolecule that comprises substantially one species of stereorepeating unit. Examples include, but are not limited to, an isotactic macromolecule, a syndiotactic macromolecule, and an atactic macromolecule. A stereoblock macromolecule is understood to be a block macromolecule composed of at least one or more stereoregular, and possibly, non-stereoregular blocks. An example is isotactic-poly(propylene)-block-atactic-poly(propylene).

An atactic polymer is a regular polymer, the molecules of which have equal numbers of the possible configurational base units in a random sequence distribution. In an atactic polymer, the polymer microstructure will contain stereocenters along the polymer backbone that have random relative configurations.

An amorphous polymer is a polymer in which there is no long-range order amongst different polymer chains that would impart crystallinity to the material.

As used herein, the term "polyolefin" comprises olefin homopolymers, co-polymers and block copolymers.

The term "about" is used herein to mean the given number plus or minus 1 to 10%.

"Living polymerization" is used herein to mean a polymerization process with substantially no chain-growth stopping reactions, such as irreversible chain transfer and chain termination. Living polymerizations allow for control over molecular weights and provide narrow molecular weight distributions. "Dormant species" is used to mean a species that cannot actively engage in propagation through chain enchainment of the monomer until it is converted into an active species through a reversible chemical process, such as a polymer chain coordinated to a neutral metal center. "Active species" is used to mean a species that can engage in propagation through chain enchainment of the monomer, such as a polymer chain coordinated to a cationic metal center. "Surrogate species" is used to define a main group metal alkyl that cannot engage in direct propagation through chain-enchainment of monomer but that can engage in reversible polymer chain transfer with an active or dormant species with a rate of chain-transfer that is at least equal in magnitude to that of the rate of propagation but preferably several times faster.

"Precision hydrocarbon" is used herein to mean a class of polyolefins that are distinguished by having programmable and architecturally-discrete carbon-carbon bonded frameworks, very low molecular weights, and extremely narrow molecular weight distributions.

Monomodal in molecular weight distribution (MWD) is used herein to mean a composition of polymers that comprise one distinct molecular weight distribution. Typically, the MWD is a range of molecular weights that may range in a number average molecular weight ($M_n$) of about 500 Da to about 500,000 Da. The MWD of a polymer can be measured using any method known to one skilled in the relevant art, for example, size exclusion chromatography and gel permeation chromatography (GPC).

"Polydispersity index" is used herein as a measure of the MWD for a given polymer composition. A polydispersity index of one refers to a monodisperse composition. The polydispersity index is a ratio of weight average molecular weight ($M_w$) to number average molecular weight ($M_n$). In one embodiment, polymer compositions made according to the present invention have low polydispersity index, for example, about 1.02-1.15. However, other embodiments of the present invention may have a low polydispersity index that is defined as being within the range of 1.01-1.2. A polydispersity index may also be within the range of 1.2-1.8 and still be classified as having been produced by the present invention if the rate of reversible chain-transfer between active and surrogate species is close in magnitude to the rate of propagation of the active species.

Coordinative chain-transfer polymerization (CCTP) employs added equivalents of a metal alkyl that can serve in the capacity of "surrogate" metal chain-growth sites. CCTP employs highly efficient and reversible chain (polymeryl group, $P_A$ and $P_B$) transfer between active transition metal propagating centers ($M_A$) and chain-growth-inactive main group metal alkyl centers ($M_B$) that proceed according to FIG. 1. If the rate constant for chain-transfer exchange between the active and inactive metal centers, $k_{ct}$, is several times greater than the rate constant for propagation, $k_p$, then both the transition and main group metal centers will effectively appear to engage in chain-growth propagation at the same rate while also maintaining all the desired features of a living polymerization (Hustad, P. D., et al., *Macromolecules* 41:4081-4089 (2008); Muller, A. H. E., et al., *Macromolecules* 28:4326-4333 (1995)). Indeed, under these conditions, $X_n$, will be governed by both the quantity of monomer consumed and the total concentration of all polymeryl groups, $P_A$ and $P_B$, that are formally engaged in active chain growth according to FIG. 1, and more precisely by: $X_n = \{[monomer]_t - [monomer]_0\}/([M-P_A)^+ + (n)(M'-P_B)]_0)$; where n is the number of equivalent polymeryl groups per main group metal (e.g. n=2 for $ZnR_2$). The molecular weight polydispersity index, D ($=M_w/M_n$), will further be approximately determined by the relative magnitudes of the rate constants for these two processes according to: $D \approx 1 + (k_p/k_{ct})$ (Müller, A. H. E., et al., *Macromolecules* 28:4326-4333 (1995)). Finally, according to the mechanism depicted in FIG. 1, the quantity of polymer product is clearly no longer capped by the amount of transition metal catalyst, but rather, on the total molar equivalents of the much less expensive and readily available main group metal alkyl ($M_B$) that is employed.

Although highly desirable for beating the 'one-chain per metal' restriction of living Ziegler-Natta polymerizations, CCTP has only been successfully demonstrated in non-living fashion for ethene polymerization and for the 'chain-shuttling' copolymerization of ethene and 1-octene employing two different single-site catalysts for the production of 'blocky' polyolefin copolymers ((for a recent review and references for CCTP of ethene using main group metal alkyls, see: Kempe, R., *Chem. Eur. J.* 13: 2764-2773 (2007); Pelletier, J. F., et al., *Angew. Chem. Int. Ed. Engl.* 35:1854-1856 (1996); Chenal, T., et al., *Polymer* 48:1844-1856 (2007); Britovsek, G. J. P., et al., *Angew. Chem. Int. Ed.* 41:489-491 (2002); Britovsek, G. J. P., et al., *J. Am. Chem. Soc.* 126: 10701-10712 (2004); van Meurs, M., et al., *J. Am. Chem. Soc.* 127:9913-9923 (2005); Rogers, J. S., et al., *Chem. Commun.* 1209-1210 (2000); Bazan, G. C., et al., *Organometallics* 20:2059-2064 (2001); Mani, G., et al., *Organometallics* 23:4608-4613 (2004); Mani, G., et al., *Angew. Chem. Int. Ed.* 43:2263-2266 (2004); Ganesan, M., et al., *J. Organomet. Chem.* 690:5145-5149 (2005); Kretschmer, W. P., et al., *Chem. Eur. J.* 12:8969-8978 (2006)); (for a 'chain-shuttling' process based on the concept of CCTP with two different catalysts and diethyl zinc ($ZnEt_2$) for the copolymerization of ethene/1-octene that produces 'blocky' poly(ethene-co-1-octene), see: Arriola, D. J., et al., *Science* 312:714-719 (2006); Hustad, P. D., et al., *Macromolecules* 40:7061-7064 (2007); Hustad, P. D., *Macromolecules* 41:4081-4089 (2008))).

For successful realization of CCTP under living or non-living conditions, it has already been convincingly demonstrated that substantial difficulties exist in identifying the right combinations of pre-catalyst, co-catalyst, main group metal alkyl chain-transfer agent, and polymerization conditions under which rapid, reversible, and highly efficient chain-transfer (including chain-shuttling between two different active propagating centers) can occur according to FIG. 1 (van Meurs, M., et al., *J. Am. Chem. Soc.* 127:9913-9923 (2005); Alfano, F., et al., *Macromolecules* 40:7736-7738 (2007)).

Living coordinative chain transfer polymerization can be considered as degenerative chain-transfer coordination polymerization, which is mechanistically distinct from a living degenerative group transfer coordination polymerization process. (Zhang, Y., et al., *J. Am. Chem. Soc.* 125:9062-9069 (2003); Zhang, Y., et al., *J. Am. Chem. Soc.* 126:7776-7777 (2004); Harney, M. B., et al., *Angew. Chem. Int. Ed.* 45:2400-2404 (2006); Harney, M. B., et al., *Angew. Chem. Int. Ed.* 45:6140-6144 (2006)).

Figure 2:
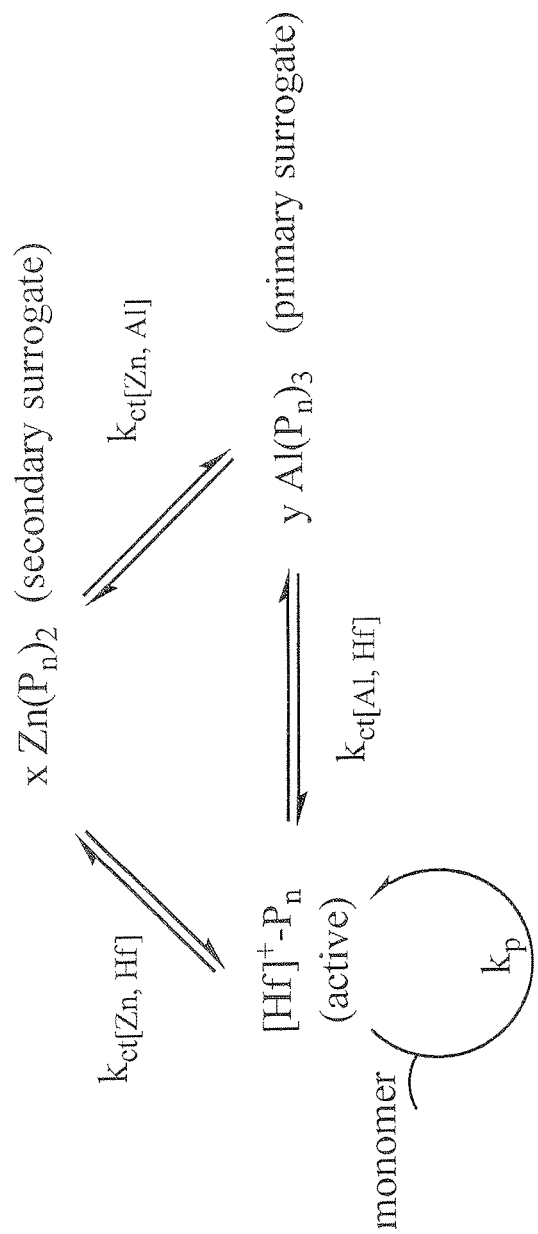
FIG. 2 shows the use of $Zn(P_n)_2$ as a secondary surrogate chain-growth species and a chain-transfer mediator to enhance the overall rate of chain-transfer between the active hafnium species ($[Hf]^+\text{—}P_n$) and the primary surrogate aluminum centers $Al(P_n)_3$ of ternary living coordinative chain-transfer polymerization. $P_n$ is a polymeryl group that is produced after multiple α-olefin insertions involving $(\eta^5\text{-}C_5Me_5)Hf(Me)_2[N(Et)C(Me)N(Et)]$.
Figure 3:
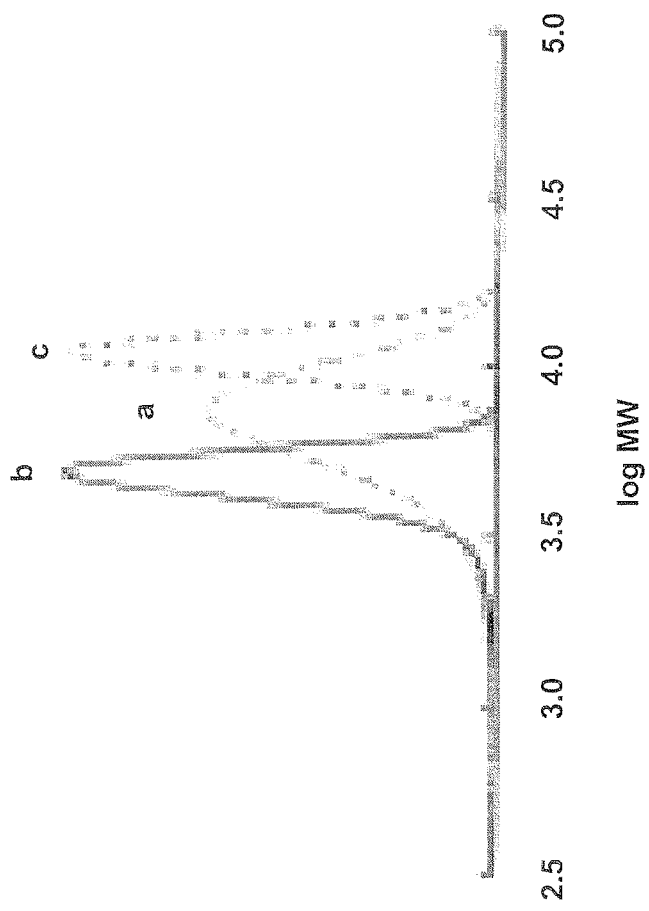
FIG. 3 shows molecular weight distributions for (a) atactic polypropene obtained from living coordinative chain-transfer polymerization of propene using 20 equivalents of $Al(iso\text{-}butyl)_3$; (b) atactic polypropene obtained from ternary living coordinative chain-transfer polymerization of propene using 18 equivalents of $Al(iso\text{-}butyl)_3$ and 2 equivalents of $ZnEt_2$; and (c) polystyrene standard ($M_n$=11,300 Da; D=1.02).
Figure 4:
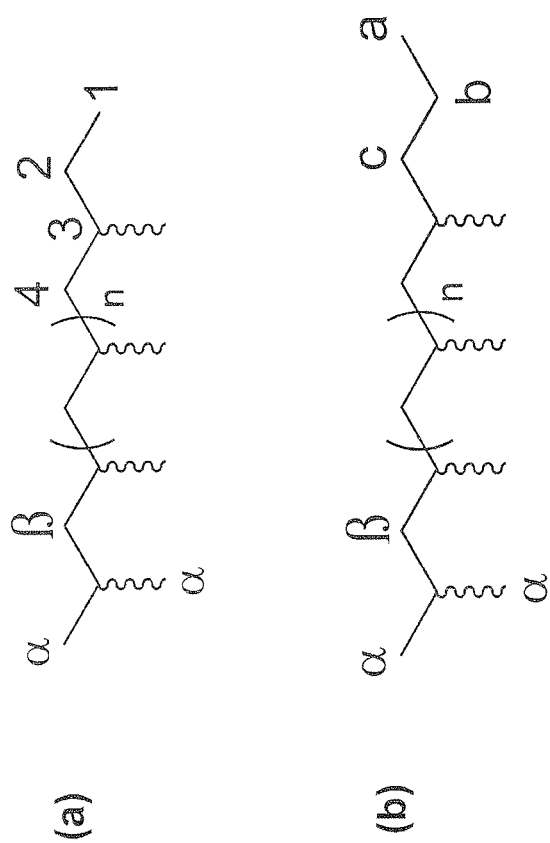
FIG. 4 is a graphic illustration of the end groups of atactic polypropene obtained from ternary living coordinative chain-transfer polymerization of propene using 10 equivalents of $Al(n\text{-}propyl)_3$ and 10 equivalents of $ZnEt_2$. The ethyl end groups in atactic polypropene from $ZnEt_2$ is shown in (a) and the n-propyl end groups from $Al(n\text{-}propyl)_3$ is shown in (b).

In order to improve upon the living coordinative chain-transfer polymerization of propene mediated by $AlEt_3$ and Al(iso-butyl)$_3$, it has been found that the addition of a third component, such as $ZnEt_2$, could act as a secondary surrogate chain-growth species, and more importantly, as a chain-transfer mediator to greatly enhance the overall rate of chain-transfer between the active hafnium species and the primary surrogate aluminum centers via the mechanism described in FIG. 2.

The present invention provides a method of producing a polyolefin composition comprising contacting a metallocene pre-catalyst, a co-catalyst, a primary surrogate, and a secondary surrogate; adding a first olefin monomer; and polymerizing said first monomer for a time sufficient to form said polyolefin.

Alternatively, after polymerizing said first monomer for a time sufficient to form a first polyolefin block, adding a second olefin monomer and polymerizing said second monomer for a sufficient time to form a polyolefin block copolymer.

Alternatively, addition of two different monomers in varying ratios, and polymerizing said mixture of monomers for a time sufficient to form a random copolymer.

Metallocene catalysts for use in the present invention include any metallocene pre-catalyst that initiates the polymerization of an olefin monomer. Specific examples include, but are not limited to single-site metallocene pre-catalyst such as those disclosed in Hlalky, et al., *J. Am. Chem. Soc.* 111:2728-2729 (1989); K. C. Jayaratne, et al., *J. Am. Chem. Soc.* 122:958-959 (2000); K. C. Jayaratne, et al., *J. Am. Chem. Soc.* 122:10490-10491 (2000); R. J. Keaton, et al., *J. Am. Chem. Soc.* 122:12909-12910 (2000) and R. J. Keaton, et al., *J. Am. Chem. Soc.* 123:6197-6198 (2001).

Illustrative but non-limiting examples of metallocene pre-catalysts for use in the present invention include dialkyl metallocenes such as bis(cyclopentadienyl)titanium dimethyl, bis(cyclopentadienyl)titanium diphenyl, bis(cyclopentadienyl)zirconium dimethyl, bis(cyclopentadienyl)zirconium diphenyl, bis(cyclopentadienyl)hafnium methyl and diphenyl, bis(cyclopentadienyl)titanium di-neopentyl, bis(cyclopentadienyl)zirconium di-neopentyl, bis(cyclopentadienyl)titanium dibenzyl, bis(cyclopentadienyl)zirconiumdibenzyl, bis(cyclopentadienyl)vanadium dimethyl; the mono alkyl metallocenes such as bis(cyclopentadienyl)titanium methyl chloride, bis(cyclopentadienyl)titanium ethyl chloride, bis(cyclopentadienyl)titanium phenyl chloride, bis(cyclopentadienyl)zirconium methyl chloride, bis(cyclopentadienyl)zirconium ethyl chloride, bis(cyclopentadienyl)zirconium phenyl chloride, bis(cyclopentadienyl)titanium methyl bromide; the trialkyl metallocenes such as cyclopentadienyl titanium trimethyl, cyclopentadienyl zirconium triphenyl, and cyclopentadienyl zirconium trineopentyl, cyclopentadienyl zirconium trimethyl, cyclopentadienyl hafnium triphenyl, cyclopentadienyl hafnium trineopentyl, and cyclopentadienyl hafnium trimethyl; monocyclopentadienyl titanocenes such as pentamethylcyclopentadienyl titanium trichloride, pentaethylcyclopentadienyl titanium trichloride, bis(pentamethylcyclopentadienyl)titanium diphenyl; the carbene represented by the formula bis(cyclopentadienyl)titanium=CH$_2$ and derivatives of this reagent; substituted bis(cyclopentadienyl)titanium (IV) compounds such as bis(indenyl)titanium diphenyl or dichloride, bis(methylcyclopentadienyl)titanium diphenyl or dihalides; dialkyl, trialkyl, tetraalkyl and pentaalkyl cyclopentadienyl titanium compounds such as bis(1, 2-dimethylcyclopentadienyl)titanium diphenyl or dichloride, bis(1,2-diethylcyclopentadienyl)titanium diphenyl or dichloride; silicon, phosphine, amine or carbon bridged cyclopentadiene complexes such as dimethyl silyldicyclopentadienyl titanium diphenyl or dichloride, methyl phosphine dicyclopentadienyl titanium diphenyl or dichloride, methylenedicyclopentadienyl titanium diphenyl or dichloride and other dihalide complexes, and the like, as well as isopropyl(cyclopentadienyl)(fluorenyl)zirconium dichloride, isopropyl(cyclopentadienyl)(octahydrofluorenyl)zirconium dichloride, diphenylmethylene(cyclopentadienyl)(fluorenyl)zirconium dichloride, diisopropylethylene(cyclopentadienyl)(fluorenyl)zirconium dichloride, diisobutylmethylene(cyclopentadienyl)(fluorenyl)zirconium dichloride, ditertbutylmethylene(cyclopentadienyl)(fluorenyl)zirconium dichloride, cyclohexylidene(cyclopentadienyl)(fluorenyl)zirconium dichloride, diisopropylmethylene(2,5-dimethylcyclopentadienyl)(fluorenyl)zirconium dichloride, isopropyl(cyclopentadienyl)(fluorenyl)hafnium dichloride, diphenylmethylene(cyclopentadienyl)(fluorenyl)hafnium dichloride, diisopropylmethylene(cyclopentadienyl)(fluorenyl)hafnium dichloride, diisobutylmethylene(cyclopentadienyl)(fluorenyl)hafnium dichloride, ditertbutylmethylene(cyclopentadienyl)(fluorenyl)hafnium dichloride, cyclohexylidene(cyclopentadienyl)(fluorenyl)hafnium dichloride, diisopropylmethylene (2,5-dimethylcyclopentadienyl)(fluorenyl)hafnium dichloride, isopropyl(cyclopentadienyl)(fluorenyl)titanium dichloride, diphenylmethylene(cyclopentadienyl)(fluorenyl)titanium dichloride, diisopropylmethylene(cyclopentadienyl)(fluorenyl)titanium dichloride, diisobutylmethylene(cyclopentadienyl)(fluorenyl)titanium dichloride, ditertbutylmethylene(cyclopentadienyl)(fluorenyl)titanium dichloride, cyclohexylidene(cyclopentadienyl)(fluorenyl)titanium dichloride, diisopropylmethylene(2,5-dimethylcyclopentadienyl)(fluorenyl)titanium dichloride, racemic-ethylene bis(1-indenyl)zirconium (IV) dichloride, racemic-ethylene bis(4,5,6,7-tetrahydro-1-indenyl)zirconium (IV) dichloride, racemic-dimethylsilyl bis(1-indenyl) zirconium (IV) dichloride, racemic-dimethylsilyl bis(4,5,6, 7-tetrahydro-1-indenyl)zirconium (IV) dichloride, racemic-1,1,2,2-tetramethylsilanylene bis(1-indenyl)zirconium (IV) dichloride, racemic-1,1,2,2-tetramethylsilanylene bis(4,5,6, 7-tetrahydro-1-indenyl)zirconium (IV) dichloride, ethylidene (1-indenyl-tetramethylcyclopentadienyl)zirconium (IV) dichloride, racemic-dimethylsilyl bis(2-methyl-4-t-butyl-1-cyclopentadienyDzirconium (IV) dichloride, racemic-ethylene bis(1-indenyl)hafnium (IV) dichloride, racemic-ethylene bis(4,5,6,7-tetrahydro-1-indenyl)hafnium (IV) dichloride, racemic-dimethylsilyl bis(1-indenyl)hafnium (IV) dichloride, racemic-dimethylsilyl bis(4,5,6,7-tetrahydro-1-indenyl)hafnium (IV) dichloride, racemic-1,1,2,2-tetramethylsilanylene bis(1-indenyl)hafnium (IV) dichloride, racemic-1,1,2,2-tetramethylsilanylene bis(4,5,6,7-tetrahydro-1 indenyl)hafnium (IV) dichloride, ethylidene (1-indenyl-2,3,4,5-tetramethyl-1-cyclopentadienyl)hafnium (IV) dichloride, racemic-ethylene bis(1-indenyl)titanium (IV) dichloride, racemic-ethylene bis(4,5,6,7-tetrahydro-1-indenyl)titanium (IV) dichloride, racemic-dimethylsilyl bis(1-indenyl)titanium (IV) dichloride, racemic-dimethylsilyl bis(4, 5,6,7-tetrahydro-1-indenyl)titanium (IV) dichloride, racemic-1,1,2,2-tetramethylsilanylene bis(1-indenyl)titanium (IV) dichloride, racemic-1,1,2,2-tetramethylsilanylene bis(4,5,6,7-tetrahydro-1-indenyl)titanium (IV) dichloride, and ethylidene (1-indenyl-2,3,4,5-tetramethyl-1-cyclopentadienyl)titanium (IV) dichloride, (N-tert-butylamido)(dimethyl)(tetramethyl-$\eta^5$-cyclopentadienyl)silane scandium hydride triphenylphosphine dimer, (N-tert-butylamido)(dimethyl)(tetramethyl-$\eta^5$-cyclopentadienyl)silane scandium hydride, (2,5-dimethyltetrahydrofuran)(N-tert-butylamido)(dimethyl)(tetramethyl-$\eta^5$-cyclopentadienyl)silane scandium bis(trimethylsilyl)methyl, (N -phenylamido)(dimethyl)(tetramethyl-$\eta^5$-cyclopentadienyl)silane scandium bis (trimethyl)methyl, (N-secbutylamido)(dimethyl)(tetramethyl-$\eta^5$-cyclopentadienyl)silane scandium bis (trimethylsilyl)methyl, (N-tert-butylamido)(dimethyl)(tetramethyl-$\eta^5$-cyclopentadienyl)silane scandium methyltribenzylphosphine, (N-tert-butylamido)(dimethyl)(tetramethyl-$\eta^5$-cyclopentadienyl)silane scandium methyl, (2,5-dimethyltetrahydrofuran)(N-tert-butylamido)(dimethyl)(tetramethyl-$\eta^5$-cyclopentadienyl)silane scandium benzyl triphenylphosphine, (N-tert-butylamido)(dimethyl)(fluorenyl)silane scandium hydride triphenylphisphine, (N-sec-dodecylamido)(dimethyl) (fluorenyl)silane scandium hydride, (2,5-dimethyltetrahydrofuran)(N-butylamido)(dimethyl)(tetramethyl-$\eta^5$-cyclopentadienyl)silane scandium bis(trimethylsilyl)methyl, (N-tert-butylphospho)(dimethyl)(tetramethyl-$\eta^5$-cyclopentadienyl)silane scandium bis (trimethyl-$\eta^5$-cyclopentadienyl)silane scandium bis (trimethylsilyl)methyl, (N-tert-butylamido)(dimethyl)(octahydrofluorenyl)silane scandium methyltriphenylphosphine, (N-tert-butylamido)(dimethyl)(indenyl)silane scandium methyl (2,5-dimethyltetrahydrofuran, and (N-tert-butylamido)(dimethyl)(tetrahydroindenyl)silane scandium 2-(N,N-dimethylamino)dibenzyl triphenylphosphine.

In one embodiment, the metallocene pre-catalyst for use in the present invention has the formula:

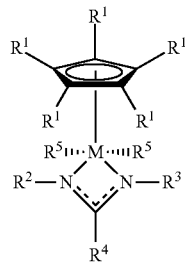

wherein the dotted lines indicate a delocalized bond;
M is Ti, Zr, Hf, V, Nb or Ta;
each $R^1$ is independently hydrogen or alkyl or two adjacent $R^1$ form an aromatic ring;
each $R^2$, $R^3$ and $R^4$ is independently alkyl, cycloalkyl, Si(alkyl)$_3$, Si(aryl)$_3$, phenyl, optionally substituted phenyl, alkylphenyl; and
each $R^5$ is halo, alkyl, cycloalkyl, aryl, or arylalkyl.

As used herein, "alkyl" refers to straight- or branched-chain hydrocarbons having from 1 to 10 carbon atoms and more preferably 1 to 8 carbon atoms, including by way of example methyl, ethyl, propyl, iso-propyl, iso-butyl and t-butyl.

"Aryl" by itself or as part of another group refers to monocyclic, bicyclic or tricyclic aromatic groups containing 6 to 14 carbon atoms in the ring position. Useful aryl groups include $C_{6-14}$ aryl, preferably $C_{6-10}$ aryl. Typical $C_{6-14}$ aryl groups include phenyl, naphthyl, indenyl, phenanthrenyl, anthracenyl, fluorenyl and biphenyl groups.

"Arylalkyl" refers to an alkyl group mentioned above substituted by a single aryl group including, by way of example, benzyl, phenethyl and naphthylmethyl.

"Alkylarylalkyl" refers to an alkyl group mentioned above substituted by a single aryl group, wherein the aryl group is further substituted by one or more alkyl groups. Examples include, without limitation, 4-methylbenzyl and 4-ethylphenethyl.

"Cycloalkyl" refers to cyclic alkyl groups containing between 3 and 8 carbon atoms having a single cyclic ring including, by way of example, cyclopropyl, cyclobutyl, cyclopentyl, cyclooctyl and the like.

"Optionally substituted phenyl" refers to a phenyl ring which may contain 1 to 5 electron donating or electron withdrawing groups. By way of example, electron-donating groups include, but are not limited to, amino, hydroxy, alkoxy, amide, aryl and alkyl. Examples of electron withdrawing groups include, but are not limited to, halo, ketone, ester, —SO$_3$H, aldehyde, carboxylic acid, cyano, nitro and ammonium.

"Alkylphenyl" refers to an alkyl group mentioned above substituted by a single phenyl group including, by way of example, benzyl, 1-phenethyl, 1-phenylpropyl, 1-phenylbutyl, 2-phenethyl, 2-phenylpropyl, 2-phenylbutyl, 3-phenylpropyl and 3-phenylbutyl.

"Halo" refers to fluoro, chloro, bromo and iodo.

"Aromatic ring" refers to an unsaturated carbocyclic group of 6 to 14 carbon atoms having a single ring (e.g., phenyl) or multiple condensed rings (e.g., naphthyl or anthryl). The metallocene catalysts of the present invention can be prepared using any suitable method known to one skilled in the relevant art. The method of synthesis of the metallocene catalysts is not critical to the invention.

In one embodiment, the metallocene catalyst is ($\eta^5$-C$_5$Me$_5$)Hf(Me)$_2$[N(Et)C(Me)N(Et)].

The co-catalyst is capable of activating the metallocene pre-catalyst.

Preferably, the co-catalyst is one of the following: (a) ionic salts of the general formula [A$^+$][—BR$^6_4$], wherein A$^+$ is Si(R$^7$)$_3$, a cationic Lewis acid or a cationic Brønsted acid, B is the element boron, R$^6$ is phenyl or an optionally substituted phenyl or (b) a boron alkyl of the general formula BR$^6_3$ and each R$^7$ is independently selected from alkyl and optionally substituted phenyl. Examples of Lewis or Brønsted acids that may be used in the practice of the invention include, but are not limited to tetra-n-butylammonium, triphenylcarbonium and dimethylanilinium cations.

Examples of co-catalysts for use in the present invention include, but are not limited to, [PhNHMe$_2$][B(C$_6$F$_5$)$_4$], [Ph$_3$C][B(C$_6$F$_5$)$_4$], and B(C$_6$F$_5$)$_3$.

The primary surrogate is capable of activating reversible chain-transfer with active transition metal-based propagating centers. Examples of a primary surrogate that may be used in the practice of this invention include Al(R$^8$)$_3$, wherein R$^8$ is an alkyl. Examples of primary surrogates for use in the present invention include AlEt$_3$, AlMe$_3$, Al(iso-butyl)$_3$, Al(n-hexyl)$_3$, Al(n-propyl)$_3$, and Al(t-butyl)$_3$. In an embodiment of the present invention, the primary surrogate is AlEt$_3$. In another embodiment, the primary surrogate is Al(iso-butyl)$_3$. In another embodiment, the primary surrogate is Al(n-propyl)$_3$.

The secondary surrogate not only acts as a chain-growth species, but also as a chain-transfer mediator to greatly enhance the overall rate of chain-transfer between the active hafnium species and the primary surrogate aluminum centers via the mechanism proposed in FIG. 2. Critical to the success of this proposal for ternary living coordinative chain-transfer polymerization, in which three different metal species act synergistically in ternary fashion, is that the relative rates and rate constants for polymeryl group exchange amongst all the metals, as well as that for chain-growth propagation at hafnium, must be of the following order: $(v_{ct}, k_{ct})_{[Zn-Hf]}$, $(V_{ct}, k_{ct})_{[Zn-Al]} \gg (v_{ct}, k_{ct})_{[Al-Hf]} > (v_p, k_p)_{[Hf]}$. Under this condition, similar approximate first-order relationships for $X_n$ and D should hold, namely: $X_n$=([monomer]$_0$–[monomer]$_t$/[(Hf)+2x(Zn)+3y(Al)]$_0$, D≈1+$k_p$/$k_{ct(obs)}$, where $k_{ct(obs)}$ is the overall apparent rate constant for chain transfer.

Examples of a secondary surrogate that may be used in the practice of this invention include Zn(R$^9$)$_2$, wherein R$^9$ is an alkyl. Examples of secondary surrogates include ZnMe$_2$, ZnEt$_2$, Zn(n-butyl)$_2$, Zn(isoamyl)$_2$, Zn(t-butyl)$_2$, Zn(neopentyl)$_2$, Zn(n-propyl)$_2$, and Zn(iso-propyl)$_2$. In an embodiment of the present invention, the secondary surrogate is ZnEt$_2$.

The method of the present invention comprises contacting a metallocene pre-catalyst, a co-catalyst, a primary surrogate, and a secondary surrogate. In one embodiment, a stoichiometric excess of primary surrogate is used. "Stoichiometric excess" is used herein to mean an amount more than an equivalent amount of the metallocene pre-catalyst and/or the co-catalyst. For example, the primary surrogate and metallocene pre-catalyst can be added together in a ratio of primary surrogate:metallocene pre-catalyst in the range of about 1:1 to about 1000:1 or about 1:1 to about 500:1. In another embodiment, the ratio of primary surrogate:metallocene pre-catalyst is in the range of about 1.1:1 to about 20:1. In another embodiment, the ratio of primary surrogate:metallocene pre-catalyst is in the range of about 1.1:1 to about 18:1. In an alternative example, the ratio of primary surrogate:metallocene pre-catalyst is about 1.1:1, 1.2:1, 1.5:1, 1.8:1, 2:1, 2.2:1, 2.5:1, 3:1, 4:1, 5:1, 10:1, 18:1, 20:1, 25:1, 50:1, 75:1, 100:1, or 200:1.

In an embodiment of the present invention, the secondary surrogate and metallocene pre-catalyst can be added together in a ratio of secondary surrogate:metallocene pre-catalyst in the range of about 1:1 to about 20:1. In another embodiment, the ratio of secondary surrogate:metallocene pre-catalyst is in the range of about 1:1 to about 10:1. In another embodiment, the ratio of secondary surrogate:metallocene pre-catalyst is in the range of about 1:1 to about 2:1. In an alternative example, the ratio of secondary surrogate:metallocene pre-catalyst is about 1:1, 1.5:1, 1.8:1, 2:1, 2.2:1, 2.5:1, 3:1, 4:1, 5:1, 10:1, 18:1, or 20:1.

In an embodiment, the metallocene pre-catalyst and co-catalyst can be added together in a ratio of metallocene pre-catalyst:co-catalyst in the range of about 1:1 to about 500:1. In an alternative example, the ratio is about 1.2:1, 1.5:1, 1.8:1, 2:1, 2.2:1, 2.5:1, 3:1, 4:1, 5:1, 10:1, 25:1, 50:1, 75:1 or 90:1. In one embodiment, the ratio of metallocene pre-catalyst:co-catalyst is about 1:1.

In an embodiment of the present invention, the primary surrogate and the secondary surrogate are added together in a ratio of primary surrogate:secondary surrogate in the range of about 1:1 to about 500:1 or about 1:1 to about 200:1. In another embodiment, the ratio of primary surrogate:secondary surrogate is in the range of about 2:1 to about 50:1. In an alternative example, the ratio is about 1.2:1, 1.5:1, 1.8:1, 2:1, 2.2:1, 2.5:1, 3:1, 4:1, 5:1, 9:1, 10:1, 19:1, 25:1, 50:1, 75:1 or 90:1.

The pre-catalyst, co-catalyst, primary surrogate, and secondary surrogate can be contacted at the same time. Alternatively, the pre-catalyst and co-catalyst can be contacted to form a first catalyst composition which is then contacted with a primary surrogate and a secondary surrogate.

The pre-catalyst, co-catalyst, primary surrogate, and secondary surrogate can be contacted neat, or in some suitable solvent. Suitable solvents for use in the present invention include inert liquid hydrocarbons that are nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose include, but are not limited to, chlorobenzene, dichlorobenzene, isopentane, hexane, cyclohexane, heptane, benzene, toluene, trifluorotoluene, pentane, octane, isooctane, dichloromethane. In one embodiment, the solvent is toluene.

The pre-catalyst, co-catalyst, primary surrogate, and secondary surrogate can be contacted at any temperature, preferably, the temperature results in the formation of an active catalyst composition for olefin polymerizations. For example, the temperature of the activation reaction is from about −25° C. to about 40° C. or from about −10° C. to about 80° C. In one embodiment, the temperature is about 20° C.

The pre-catalyst, co-catalyst, primary surrogate, and secondary surrogate can be contacted for any length of time, as long as the activation reaction results in an active catalyst composition for olefin polymerizations. For example, the activation reaction can be performed for a time of about 1 minute to about 50 hours or about 30 minutes to about 5 hours. Alternatively, monomer may be added immediately following the contacting of the metallocene pre-catalyst, co-catalyst, primary surrogate, and secondary surrogate. In one embodiment, the activation reaction is performed for about 2 hours. In another embodiment, the activation reaction is performed for about 4 hours.

The pre-catalyst, co-catalyst, primary surrogate, and secondary surrogate can be contacted at any pressure. In one embodiment, the pressure is between about 0 psi to about 40 psi. In another embodiment, the pressure is about 5 psi.

Olefin monomers for use in the invention include, but are not limited to, ethene, propene, 1-butene, 1-pentene, 1-hexene, 1-heptene, 1-octene, styrene, butadiene, isoprene, 3-methylbutene, 3-methyl-1-pentene, vinylcyclohexane, vinylcyclobutane, vinylcyclopentane, vinylcyclooctane, 1-decene, enantiomerically pure β-citronellene, 3,5,5-trimethyl-1-hexene, 4-methyl-1-pentene or cyclic olefins such as cyclobutene, cyclopentene, cyclohexene, cyclooctene, and alkyl or aryl-substituted cyclic olefins. Olefin monomers for use also include conjugated or non-conjugated dienes, such as linear, branched, or cyclic hydrocarbon dienes having from about 4 to about 20, preferably 4 to 12, carbon atoms, including those dienes having the formula:

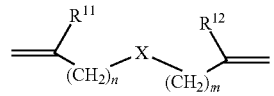

wherein X=CH$_2$, CO, N(R$^{13}$), O or S;
R$^{11}$, R$^{12}$ and R$^{13}$ are each independently H, alkyl or phenyl; and
n and m are each independently an integer from 0-5.

Dienes include 1,4-pentadiene, 1,5-hexadiene, 5-vinyl-2-norbornene, 1,7-octadiene, vinylcyclohexane, dicyclopentadiene, butadiene, isobutylene, isoprene and ethylidene norbornene.

In an embodiment of the present invention, the first olefin monomer is propene.

The time required for forming the polyolefin varies depending on the olefin monomer, temperature of reaction, reactant concentrations, and other conditions, and can be for any length of time, as long as a polymer is formed. For example, the polymerization of the first olefin can be performed for a time of about 1 minute to about 50 hours or about 30 minutes to about 5 hours.

The second olefin monomer can be any polymerizable olefin or diene and it can be added at the same time as the first monomer in which case a random polyolefin copolymer will be obtained. Alternatively, the second olefin can be added after sufficient time for the first monomer to be polymerized in which case a block polyolefin copolymer will be obtained. The ratio of first monomer to second monomer can be, but is not limited to, the range of 1:100 to 100:1. In one example, the first olefin is propene and the second olefin is 1-octene. In another example, the first olefin in ethene and the second olefin is propene.

In an embodiment, polymerization methods of the present invention are flexible and allow for the manufacture of polyolefin compositions having various molecular weights. The molecular weights that are given, therefore, are not meant to be limiting. For example, polyolefin compositions of the present invention have number average molecular weight ($M_n$) greater that about 500. More particularly, the polyolefin compositions have number average molecular weight of about 1,000 to about 500,000. Methods of determining number average molecular weight of polyolefin compositions are well known to one of ordinary skill in the art. For example, gel permeation chromatography (GPC) may be used.

Polymer compositions made according to the present invention have low polydispersity index, for example, about 1.01-1.15. However, other embodiments of the present invention may have a low polydispersity index that is defined as being within the range of 1.01-1.2. A polydispersity index may also be within the range of 1.2-1.8 and still be classified as having been produced by the present invention if the rate of reversible chain-transfer between active and surrogate species is close in magnitude to the rate of propagation of the active species.

Having now generally described this invention, the same will be understood by reference to the following examples which are provided herein for purposes of illustration only and are not intended to be limiting unless otherwise specified.

EXAMPLES

All manipulations were performed under an inert atmosphere of dinitrogen using either standard Schlenk techniques or a Vacuum Atmospheres glovebox. Dry, oxygen-free solvents were employed throughout. Toluene was distilled from sodium. Toluene-$d_8$ was vacuum transferred from sodium potassium amalgam (NaK) prior to use for NMR spectroscopy. Polymer grade propene was purchased from Matheson Trigas, and passed through activated Q5 and molecular sieves (4 Å). ($\eta^5$-$C_5Me_5$)Hf(Me)$_2$[N(Et)C(Me)N(Et)] was prepared according to previously reported procedures. [PhNHMe$_2$][B(C$_6$F$_5$)$_4$] was purchased from Boulder Scientific. [Ph$_3$C][B(C$_6$F$_5$)$_4$] was obtained from Strem Inc. and used without further purification.

Gel permeation chromatography (GPC) analyses were performed using a Viscotek GPC system equipped with a column oven and differential refractometer both maintained at 45° C. and four columns also maintained at 45° C. Tetrahydrofuran was used as the eluant at a flow rate of 1.0 mL/min. $M_n$, $M_w$ and $M_w/M_n$ values were obtained using a Viscotek GPC with OmniSEC software (conventional calibration) and ten polystyrene standards ($M_n$=580 Da to 3,150 kDa) (Polymer Laboratories). $^{13}$C {$^1$H} NMR spectra were recorded at 150 MHz, using 1,1,2,2-tetrachloroethane-$d_2$ as the solvent at 90° C.

TABLE 1

Results for LCCTP and t-LCCTP of propene.

| | AlR$_3$ | ZnEt$_2$ | $t_p$ | $T_p$ | Yield | $M_n$ | |
|---|---|---|---|---|---|---|---|
| | R | eq$^a$ | eq$^a$ | (h) | (° C.) | (g) | (kDa) | $Đ^b$ |
| LCCTP |
| 1 | — | — | 20 | 2 | 0 | 4.2 | 8.75 | 1.04 |
| 2 | Et | 20 | — | 2 | 0 | 3.9 | 5.21 | 1.19 |
| 3 | iBu | 20 | — | 4 | 20 | 4.6 | 6.00 | 1.19 |
| 4 | iBu | 100 | — | 16 | 20 | 2.6 | 0.82 | 1.21 |
| t-LCCTP |
| 5 | Et | 10 | 10 | 2 | 0 | 4.4 | 7.31 | 1.02 |
| 6 | nPr | 10 | 10 | 2 | 0 | 2.0 | 2.88 | 1.05 |
| 7 | iBu | 10 | 10 | 2 | 0 | 1.2 | 1.84 | 1.07 |
| 8 | iBu | 18 | 2 | 4 | 20 | 3.1 | 4.53 | 1.04 |
| 9 | iBu | 190 | 10 | 72 | 20 | 88.0 | 0.58$^c$ | 1.10 |
| 10$^d$ | iBu | 18 | 2 | 4 | 20 | .8 | 1.27 | 1.10 |
| 11$^d$ | iBu | 20 | 0 | 4 | 20 | 1.4 | 2.31 | 1.46 |

$^a$Molar equivalents relative to [($\eta^5$-C$_5$Me$_5$)Hf(Me)[N(Et)C(Me)N(Et)]][B(C$_6$F$_5$)$_4$].
$^b$Determined by GPC analysis.
$^c$Determined by NMR end-group analysis.
$^d$t-LCCTP carried out in the presence of 500 equivalents of octene.

Example 1

Typical Procedure for Ternary LCCTP

In a 250 mL Schlenk flask, to a solution of the co-catalyst [Ph$_3$C][B(C$_6$F$_5$)$_4$] (18.5 mg, 20 µmol) in 20 mL of toluene at 20° C. was added ($\eta^5$-C$_5$Me$_5$)Hf(Me)$_2$[N(Et)C(Me)N(Et)] (9.1 mg, 20 µmol) and the mixture stirred for 10 minutes to generate {($\eta^5$-C$_5$Me$_5$)Hf(Me)$_2$[N(Et)C(Me)N(Et)]}[B(C$_6$F$_5$)$_4$]. Al(iso-butyl)$_3$ (476 mg, 18 equiv) as a 15% wt solution in toluene and ZnEt$_2$ (33 mg, 2 equiv) as a 15% wt (1.1 M) solution in toluene were added and stirred for 10 minutes. The flask was then pressurized to 5 psi with propene and the pressure was maintained for 4 hours with stirring before quenching with 1.0 mL of methanol. The toluene solution was precipitated into 600 mL of acidic methanol (10% concentrated HCl) to isolate the polypropene material. The final product was collected and dried overnight in vacuo. Yield: 3.1 g. GPC analysis: $M_w$=4,710 Da; $M_n$=4,530 Da; Đ=1.04.

The upper half of Table 1 summarizes the results of LCCTP of propene using {($\eta^5$-C$_5$Me$_5$)Hf(Me)$_2$[N(Et)C(Me)N(Et)]}[B(C$_6$F$_5$)$_4$] and multiple equivalents of ZnEt$_2$, AlEt$_3$, and Al(iso-butyl)$_3$ as conducted using previously reported procedures (see International Application Publication No. WO 2009/061499). Entry 1 of Table 1 serves as a frame of reference where 1 equivalent of {($\eta^5$-C$_5$Me$_5$)Hf(Me)$_2$[N(Et)C(Me)N(Et)]}[B(C$_6$F$_5$)$_4$] and 20 equivalents of ZnEt$_2$ in toluene provided, after 2 hours at 0° C. and 5 psi of propene, an atactic polypropene material for which the yield and $M_n$ values are consistent with both ethyl groups of ZnEt$_2$ being accessible and engaged in rapid and reversible chain-transfer with the active transition-metal propagating species and gave a Đ of 1.04. Upon replacing ZnEt$_2$ with AlEt$_3$ (entry 2, Table 1), similar results were obtained under identical conditions and again based on the yield and the value of $M_n$, it can be concluded that all three ethyl groups of AlEt$_3$ successfully engaged in reversible chain-transfer. Furthermore, end-group analysis of this atactic polypropene material by $^{13}$C NMR spectroscopy (150 MHz, 1,1,2,2-tetrachloroethane-$d_2$, 90° C.) revealed the absence of terminal vinyl resonances due to irreversible β-hydrogen transfer chain-termination, thereby providing significant support for the living character of this polymerization. However, the larger Đ value of 1.19 for this material obtained with AlEt$_3$ is indicative of a smaller rate constant for hafnium-aluminum polymeryl group exchange, relative to that for hafnium-zinc chain transfer, or more specifically, $k_{ct[Zn-Hf]} > k_{ct[Al-Hf]}$ according to FIG. 2. Using Al(iso-butyl)$_3$ (entry 3, Table 1), required both an increase in temperature and time in order to obtain an appreciable quantity of atactic polypropene. Efforts to scale-up this reaction using 100 equivalents of Al(iso-butyl)$_3$ (entry 4, Table 1) required an exceedingly long polymerization time of 16 hours to provide a small amount of product that had a D value of 1.21. Furthermore, using Al(iso-butyl)$_3$, it was noted that a long induction period of at least one hour was observed prior to the onset of living coordinative chain-transfer.

Figure 5:
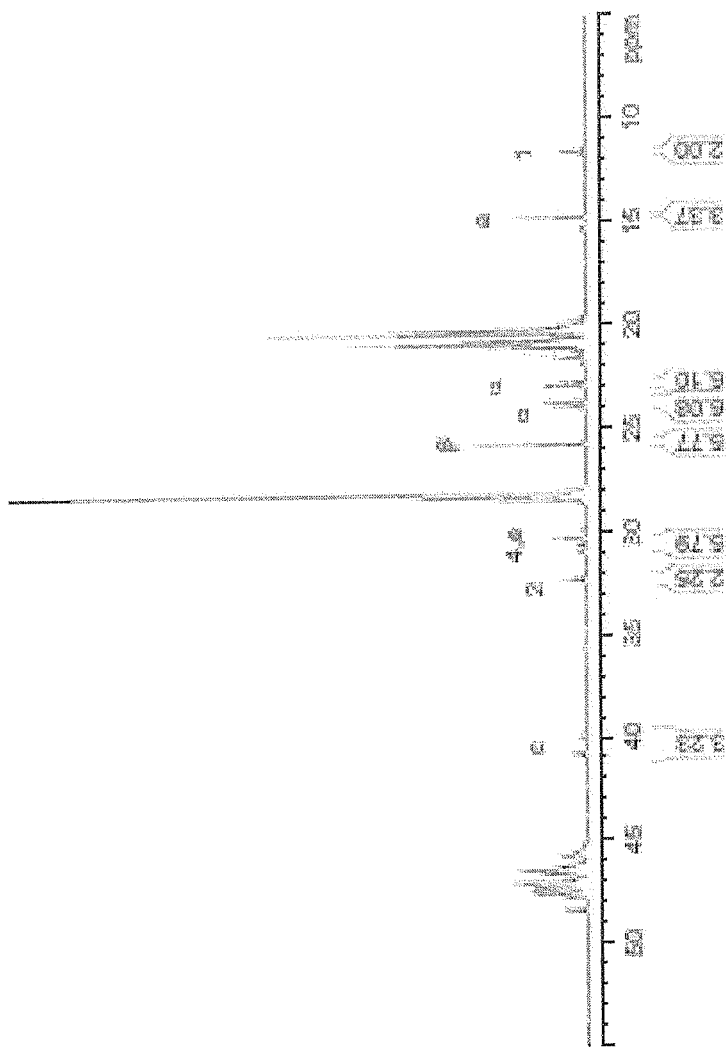
FIG. 5 is a $^{13}C\ \{^1H\}$ NMR spectrum for atactic polypropene obtained from ternary living coordinative chain-transfer polymerization of propene using 10 equivalents of $Al(n\text{-}propyl)_3$ and 10 equivalents of $ZnEt_2$.
Figure 6:
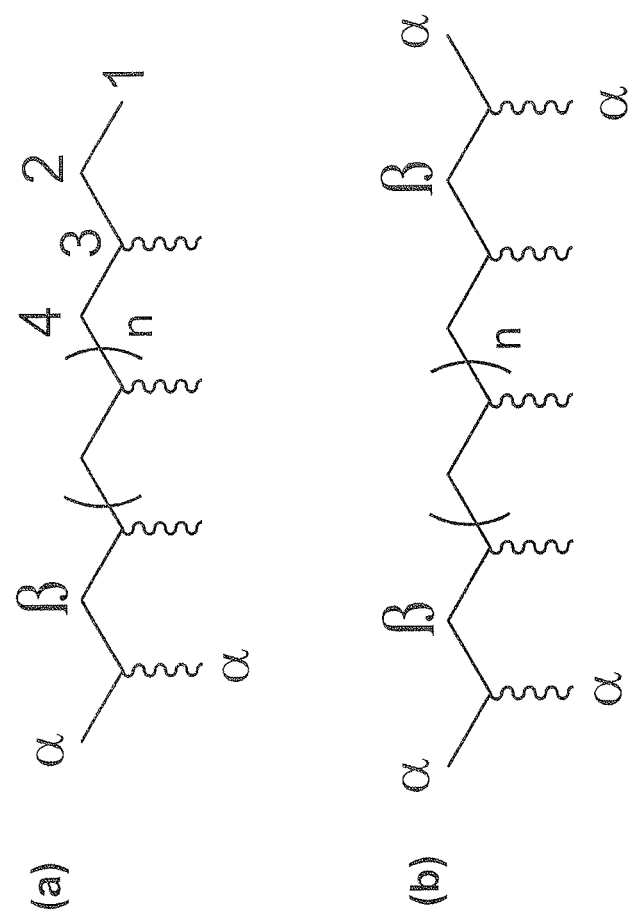
FIG. 6 is a graphic illustration of the end groups of atactic polypropene obtained from ternary living coordinative chain-transfer polymerization of propene using 10 equivalents of $Al(iso\text{-}butyl)_3$ and 10 equivalents of $ZnEt_2$. The ethyl end groups in atactic polypropene from $ZnEt_2$ are shown in (a) and the isobutyl end groups from $Al(iso\text{-}butyl)_3$ are shown in (b).
Figure 7:
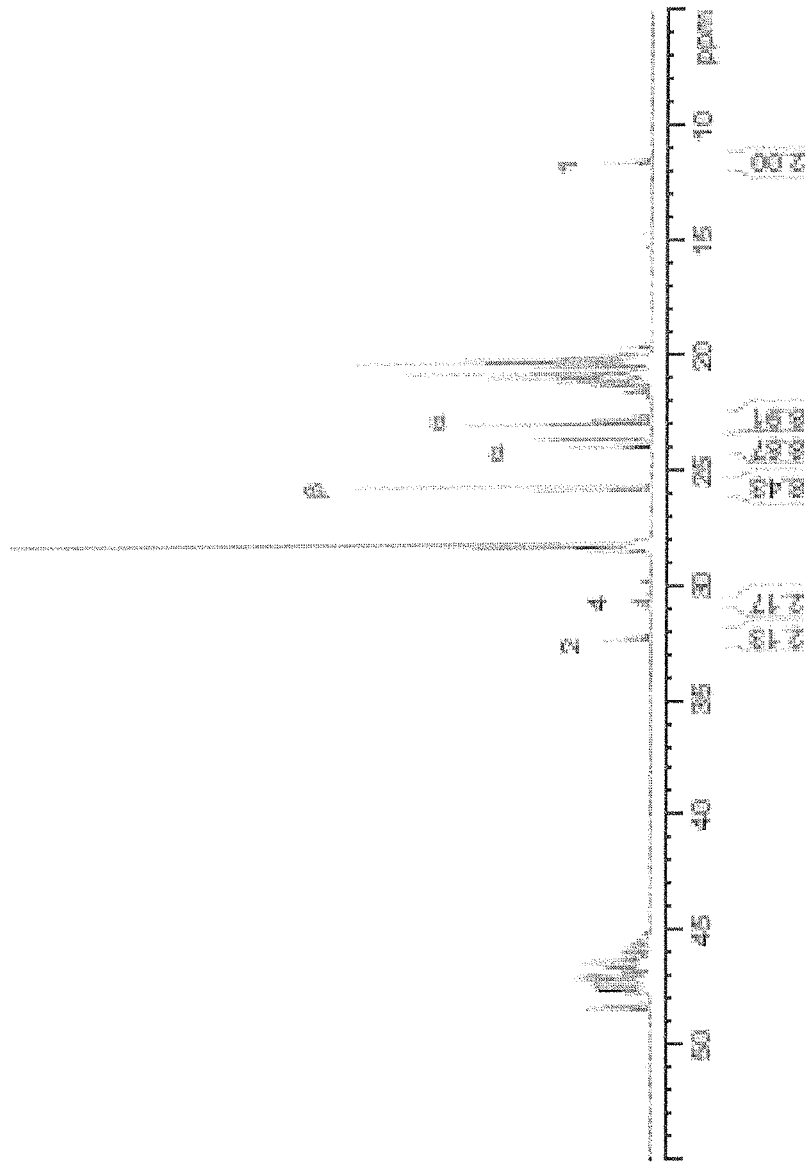
FIG. 7 is a $^{13}C\ \{^1H\}$ NMR spectrum for atactic polypropene obtained from ternary living coordinative chain-transfer polymerization of propene using 10 equivalents of $Al(iso\text{-}butyl)_3$ and 10 equivalents of $ZnEt_2$.
Figure 8:
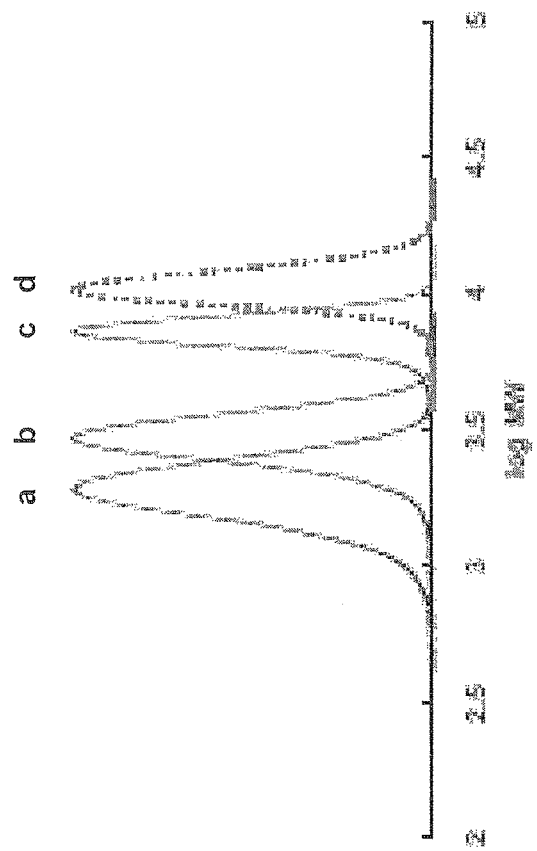
FIG. 8 shows molecular weight distributions for (a) atactic polypropene obtained from ternary living coordinative chain-transfer polymerization of propene using 10 equivalents of $Al(iso\text{-}butyl)_3$ and 10 equivalents of $ZnEt_2$; (b) atactic polypropene obtained from ternary living coordinative chain-transfer polymerization of propene using 10 equivalents of $Al(n\text{-}propyl)_3$ and 10 equivalents of $ZnEt_2$; (c) atactic polypropene obtained from ternary living coordinative chain-transfer polymerization of propene using 10 equivalents of $Al(Et)_3$ and 10 equivalents of $ZnEt_2$; and (d) polystyrene standard ($M_n$=11,300 Da; D=1.02).
Figure 9:
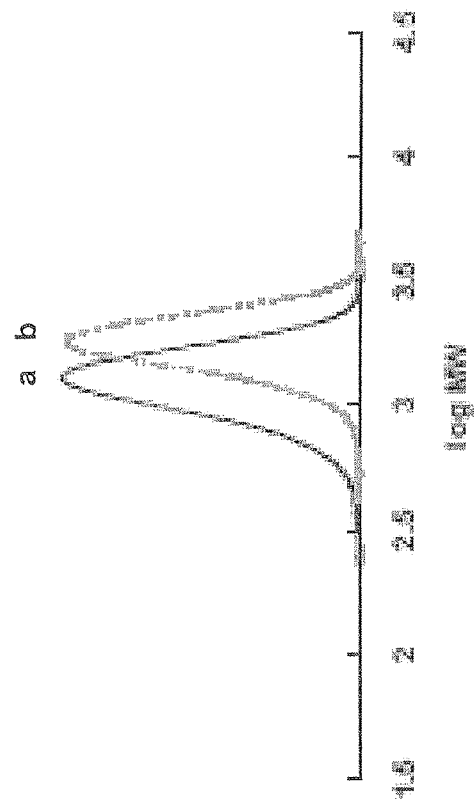
FIG. 9 shows molecular weight distributions for (a) atactic polypropene obtained from ternary living coordinative chain-transfer polymerization of propene using 190 equivalents of $Al(iso\text{-}butyl)_3$ and 10 equivalents of $ZnEt_2$; and (b) polystyrene standard ($M_n$=1,700 Da; D=1.06).
Figure 10:
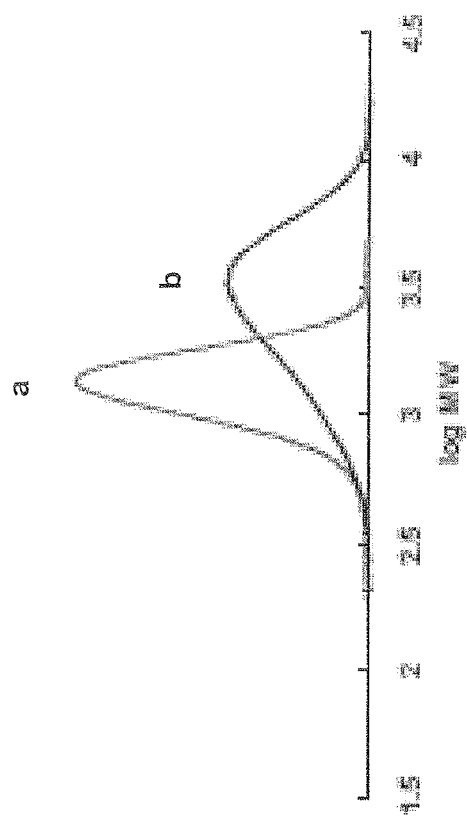
FIG. 10 shows molecular weight distributions for (a) atactic polypropene obtained from ternary living coordinative chain-transfer polymerization of propene carried out in the presence of 500 equivalents of 1-octene using 18 equivalents of $Al(iso\text{-}butyl)_3$ and 2 equivalents of $ZnEt_2$; and (b) atactic polypropene obtained from ternary living coordinative chain-transfer polymerization of propene carried out in the presence of 500 equivalents of 1-octene using 20 equivalents of $Al(iso\text{-}butyl)_3$.

As shown in Table 1, the introduction of ZnEt$_2$ into the AlEt$_3$, Al(iso-butyl)$_3$, and Al(n-propyl)$_3$ mediated LCCTP of propene in toluene at 0° C. for two hours and 5 psi had a desired favorable influence on the values for all the values of yield, M$_n$, and D. More specifically, when 10 equivalents each of AlEt$_3$ and ZnEt$_2$ were initially employed, both the yield and M$_n$ values of the isolated atactic polypropene were found to be consistent with extremely rapid and reversible chain-transfer occurring amongst all three metal species, and remarkably, the polydispersity of this material was shown to be extremely narrow with a D value of 1.02 (entry 5, Table 1). Similar results were obtained when Al(n-propyl)$_3$ (entry 6, Table 1) and Al(iso-butyl)$_3$ (entry 7, Table 1) were employed as the primary surrogates. As shown in FIG. 5 and FIG. 7, end-group analysis by $^{13}$C NMR spectroscopy established that all three alkyl groups of Al(n-propyl)$_3$ and Al(iso-butyl)$_3$ and the two ethyl groups of ZnEt$_2$ were incorporated into the respective atactic polypropene materials at the theoretical level and ratio in each case. Furthermore, as shown by entries 5, 6, and 7 in Table 1, as the steric size of the R group in AlR$_3$ increases in the order, Et<n-propyl<iso-butyl, a commensurate decrease in the apparent overall rate of ternary LCCTP (t-LCCTP) is observed. As shown in entries 5-7 of Table 1, this steric size increase also showed an increase in D values. While not wishing to be bound by theory, it is believed that this trend arises from differences in the rates for initial chain-transfer.

As is shown by entry 8 of Table 1, production of atactic polypropene can be achieved using a minimal amount of ZnEt$_2$. Therefore, with 10 mol % of ZnEt$_2$ serving in the capacity of a chain-transfer mediator and secondary surrogate, the ternary LCCTP of propene can be effectively and efficiently achieved using 18 equivalents of Al(iso-butyl)$_3$ as the primary surrogate in toluene under near ambient conditions to produce an atactic polypropene material of very narrow polydispersity (D=1.04).

Example 2

Scaled-Up Ternary LCCTP of Propene (Entry 9, Table 1)

In a 500 mL Schlenk flask, to a solution of the co-catalyst [Ph$_3$C][B(C$_6$F$_5$)$_4$] (221.4 mg, 0.24 mmol) in 300 mL of toluene at 25° C. was added {($\eta^5$-C$_5$Me$_5$)Hf(Me)$_2$[N(Et)C(Me)N(Et)]} (109.7 mg, 0.24 mmol) and the mixture was stirred for 10 minutes. Al(i-Bu)$_3$ (9.04 g, 190 equiv) and ZnEt$_2$ (1.98 g, 10 equiv) as 15% wt (1.1 M) solution in toluene were added and stirred for 10 minutes. The flask was then pressurized to 5 psi with propene and the pressure was maintained for 72 hours with stirring before quenching with 10.0 mL of methanol. The toluene solution was precipitated into 1600 mL, of acidic methanol to isolate the atactic polypropene. The crude product was redissolved in toluene and passed through silica gel, followed by re-precipitating into 800 mL acidic methanol. The final product was collected and dried overnight in vacuo. Yield: 88.3 g. GPC analysis: M$_w$=1,310 Da; M$_n$=1,190 Da; D=1.10. $^{13}$C NMR spectra end-group analysis: M$_n$=580 Da.

Figure 11:
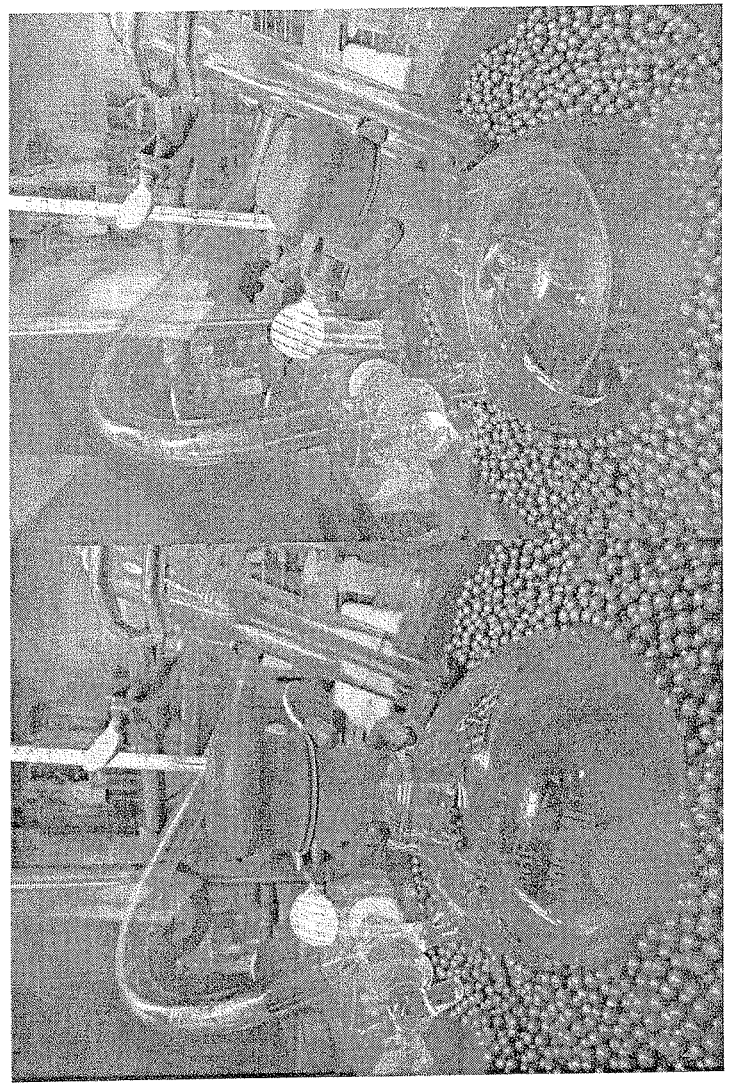
FIG. 11 shows pictures of scaled-up ternary living coordinative chain-transfer polymerization of propene using 190 equivalents of $Al(iso\text{-}butyl)_3$ and 10 equivalents of $ZnEt_2$. The reaction mixture is shown before (a) and after (b) the polymerization reaction.

Therefore, this ternary LCCTP of propene could be successfully scaled in volume by simply employing 190 equivalents of Al(iso-butyl)$_3$ with as little as only 5 mol % (10 equivalents) of ZnEt$_2$ in toluene at near ambient conditions to provide 88 grams of the new precision hydrocarbon-based 'white' oil represented by atactic polypropene with a targeted low molecular weight and very narrow polydispersity. In order to obtain an equal quantity of this precision hydrocarbon material through traditional living coordination polymerization, 179 g of {($\eta^5$-C$_5$Me$_5$)Hf(Me)$_2$[N(Et)C(Me)N(Et)]}[B(C$_6$F$_5$)$_4$] would have been required as compared to the 0.3 g quantity that was employed for ternary LCCTP. Furthermore, this ternary LCCTP of propene was carried out at ambient temperature over a period of 72 hours without any apparent degradation in product polydispersity as shown in FIG. 11.

Example 3

Typical Procedure for Ternary LCCTP Copolymerization

In a 250 mL Schlenk flask, to a solution of the co-catalyst [Ph$_3$C][B(C$_6$F$_5$)$_4$] (18.5 mg, 20 µmol) in 20 mL of toluene at 20° C. was added {($\eta^5$-C$_5$Me$_5$)Hf(Me)$_2$[N(Et)C(Me)N(Et)]}[B(C$_6$F$_5$)$_4$] (9.1 mg, 20 µmol) and the mixture stirred for 10 minutes. Al(iso-butyl)$_3$ (476 mg, 18 equiv) as 15% wt solution in toluene and ZnEt$_2$ (33 mg, 2 equiv) as 15% wt (1.1 M) solution in toluene were added and stirred for 10 minutes. To the flask was added 1-octene (1.12 g, 500 equiv) and it was pressurized to 5 psi with propene and the pressure was maintained for 4 hours with stirring before quenching with 1.0 mL of methanol. The toluene solution was precipitated into 600 mL of acidic methanol to isolate atactic polypropene. The final product was collected and dried overnight in vacuo. Yield: 0.84 g. GPC analysis: M$_w$=1,400 Da; M$_n$=1,270 Da; D=1.10.

As shown in entry 10 of Table 1, ternary LCCTP can be successfully extended to copolymerizations. In entry 10, 10 mol % of ZnEt$_2$ in combination with 18 equivalents of Al(iso-butyl)$_3$ efficiently provided a precision hydrocarbon material comprised of a targeted low molecular weight random copolymer of propene and 1-octene of very narrow polydispersity (M$_n$=820 Da; D=1.10). In the absence of ZnEt$_2$ (entry 11, Table 1), standard LCCTP provides a similar material of inferior polydispersity (D=1.46).

Example 4

End-Group Analysis Using $^{13}$C NMR Spectroscopy $^{13}$C NMR spectroscopy was used to directly investigate the ratio of different atactic polypropene chain-end structures from alkyl groups of AlR$_3$ and ZnEt$_2$. As shown in FIG. 5 (entry 6, Table 1), 3/10 of the polymer chain-ends had were of the n-propyl type, 1/5 of the chain-ends were of the ethyl type, and 1/2 of the chain-ends were of the iso-butyl type.

As shown in FIG. 7 (entry 7, Table 1), 4/5 of the polymer chain ends were of the iso-butyl type and 1/5 of the chain ends were of the ethyl type. This proves that all alkyl groups on aluminum undergo chain-transfer in ternary LCCTP.

Having now fully described this invention, it will be understood by those of ordinary skill in the art that the same can be performed within a wide and equivalent range of conditions, formulations and other parameters without affecting the scope of the invention or any embodiment thereof. All patents, patent applications, and publications cited herein are fully incorporated by reference herein in their entirety.

What is claimed is:

1. A method of producing a polyolefin composition comprising:
   (a) contacting a metallocene pre-catalyst, a co-catalyst, of Al(R$^8$)$_3$, wherein R$^8$ is a C$_1$-C$_{10}$ alkyl, and Zn(R$^9$)$_2$, wherein R$^9$ is a C$_1$-C$_{10}$ alkyl;
   (b) adding a first olefin monomer; and
   (c) polymerizing by ternary living coordinative chain transfer said first olefin monomer for a time sufficient to form said polyolefin, wherein Al(R$^8$)$_3$ and Zn(R$^9$)$_2$ are added in a ratio of about 1.1:1 to about 100:1.

2. The method of claim 1, wherein R$^8$ is selected from the group consisting of ethyl, methyl, iso-butyl, n-hexyl, n-propyl, and t-butyl.

3. The method of claim 2, wherein R$^8$ is iso-butyl.

4. The method of claim 2, wherein R$^8$ is ethyl.

5. The method of claim 2, wherein R$^8$ is n-propyl.

6. The method of claim 1, wherein R$^9$ is selected from the group consisting of methyl, ethyl, n-butyl, isoamyl, t-butyl, neopentyl, n-propyl, and iso-propyl.

7. The method of claim 6, wherein R$^9$ is ethyl.

8. The method of claim 1, wherein said ratio is about 9:1.

9. The method of claim 1, wherein said ratio is about 19:1.

10. The method of claim 1, wherein said metallocene pre-catalyst is ($\eta^5$-C$_5$Me$_5$)Hf(Me)$_2$[N(Et)C(Me)N(Et)].

11. The method of claim 1, wherein said co-catalyst is selected from the group consisting of [PhNMe$_2$H][B(C$_6$F$_5$)$_4$], [PhNMe$_2$H][B(C$_6$F$_5$)$_3$Me], and B(C$_6$F$_5$)$_3$.

12. The method of claim 1, wherein the Al(R$^8$)$_3$ and Zn(R$^9$)$_2$ are contacted with the metallocene pre-catalyst and the co-catalyst in an inert solvent.

13. The method of claim 12, wherein said solvent is toluene.

14. The method of claim 1, wherein the Al(R$^8$)$_3$, the Zn(R$^9$)$_2$, the metallocene pre-catalyst, and the co-catalyst are contacted at a temperature of about −20° C. to about 25° C.

15. The method of claim 1, wherein the first olefin monomer is selected from the group consisting of ethene, propene, 1-butene, 1-pentene, 1-hexene, 1-heptene, 1-octene, styrene, butadiene, isoprene, 3-methylbutene, 3-methyl-1-pentene, vinylcyclohexane, vinylcyclobutane, vinylcyclopentane, vinylcyclooctane, 1-decene, enantiomerically pure β-citronellene, 3,5,5-trimethyl-1-hexene, cyclopentene, vinylcyclohexene, and 4-methyl-1-pentene.

16. The method of claim 1, wherein the first olefin monomer is selected from the group consisting of ethene, propene, 1-hexene, 1-octene, and 1,5-hexadiene.

17. The method of claim 1, wherein the polyolefin is an atactic polyolefin having a polydispersity index of about 1.01-1.15.

18. The method of claim 1, wherein the metallocene pre-catalyst is ($\eta^5$-C$_5$Me$_5$)Hf(Me)$_2$[N(Et)C(Me)N(Et)], R$^8$ is ethyl, R$^9$ is ethyl, and the first olefin monomer is propene.

19. The method of claim 1, wherein the metallocene pre-catalyst is ($\eta^5$-C$_5$Me$_5$)Hf(Me)$_2$[N(Et)C(Me)N(Et)], R$^8$ is n-propyl, R$^9$ is ethyl, and the first olefin monomer is propene.

20. The method of claim 1, wherein the metallocene pre-catalyst is ($\eta^5$-C$_5$Me$_5$)Hf(Me)$_2$[N(Et)C(Me)N(Et)], R$^8$ is iso-butyl, R$^9$ is ethyl, the first olefin monomer is propene.

21. The method of claim 20, wherein the ratio of Al(R$^8$)$_3$ to Zn(R$^9$)$_2$ is from about 9:1 to about 19:1.

22. The method of claim 1, further comprising adding a second olefin monomer; and polymerizing said second monomer for a time sufficient to form a polyolefin block copolymer.

23. The method of claim 22, wherein said second olefin monomer is selected from the group consisting of ethene, propene, 1-butene, 1-pentene, 1-hexene, 1-heptene, 1-octene, styrene, butadiene, isoprene, 3-methylbutene, 3-methyl-1-pentene, vinylcyclohexane, vinylcyclobutane, vinylcyclopentane, vinylcyclooctane, 1-decene, enantiomerically pure β-citronellene, 3,5,5-trimethyl-1-hexene, and 4-methyl-1-pentene.

24. The method of claim 22, wherein said polyolefin block copolymer is an atactic living polyolefin.

25. The method of claim 22, wherein said polyolefin block copolymer comprises a diblock copolymer having the formula: atactic-poly(first olefin)-co-poly(second olefin).

26. The method of claim 22, wherein said polyolefin block copolymer has a polydispersity index of about 1.02-1.2.

27. The method of claim 22, wherein said polyolefin block copolymer is monomodal.

28. The method of claim 22, wherein the metallocene pre-catalyst is ($\eta^5$-C$_5$Me$_5$)Hf(Me)$_2$[N(Et)C(Me)N(Et)], R$^8$ is iso-butyl, R$^9$ is ethyl, the first olefin monomer is propene, and the second olefin monomer is 1-octene.

29. The method of claim 28, wherein the ratio of Al(R$^8$)$_3$ to Zn(R$^9$)$_2$ is about 9:1.

* * * * *